(12) United States Patent
Poulos

(10) Patent No.: US 10,500,343 B2
(45) Date of Patent: Dec. 10, 2019

(54) SYRINGE

(71) Applicant: Jay-Nik Pty Ltd (ACN 620 076 253), Davenport, Tasmania (AU)

(72) Inventor: George Poulos, Forth (AU)

(73) Assignee: JAY-NIK PTY LTD (ACN 620 076 253), Devonport, Tasmania (AU)

( * ) Notice: Subject to any disclaimer, the term of this patent is extended or adjusted under 35 U.S.C. 154(b) by 123 days.

(21) Appl. No.: 15/528,762

(22) PCT Filed: Nov. 21, 2014

(86) PCT No.: PCT/AU2014/001066
§ 371 (c)(1),
(2) Date: May 22, 2017

(87) PCT Pub. No.: WO2016/004452
PCT Pub. Date: Jan. 14, 2016

(65) Prior Publication Data
US 2017/0340828 A1    Nov. 30, 2017

(51) Int. Cl.
*A61M 5/315* (2006.01)
*A61M 5/00* (2006.01)
(Continued)

(52) U.S. Cl.
CPC ........ *A61M 5/31511* (2013.01); *A61M 5/002* (2013.01); *A61M 5/3129* (2013.01);
(Continued)

(58) Field of Classification Search
CPC .. A61J 1/2096; A61J 3/072; A61J 1/16; A61J 1/20; A61M 5/1782; A61M 2005/1426;
(Continued)

(56) References Cited

U.S. PATENT DOCUMENTS 1,348,412 A    8/1920    Harriman
3,473,646 A    10/1969   Burke
(Continued)

FOREIGN PATENT DOCUMENTS

WO    WO 1998/019723 A1    5/1998
WO    WO 01/00261 A1       1/2001
(Continued)

OTHER PUBLICATIONS

Examination Report No. 1, dated Mar. 10, 2017, in Australian Patent Application No. 2014400365.
(Continued)

*Primary Examiner* — Nathan R Price
*Assistant Examiner* — Melissa A Snyder
(74) *Attorney, Agent, or Firm* — Knobbe, Martens, Olson & Bear, LLP

(57) ABSTRACT

This invention relates to a method of identifying an accurate dosage of medicine in a dosage chamber of a syringe including the steps of providing an accurate dosage of a detailed single dosage medicine for insertion into a dosage chamber of a syringe; identifying the accurate dosage of medicine in the dosage chamber by retaining a notifier of the accurate dosage; securing the notifier with the syringe wherein the accurate dosage of medicine in a dosage chamber of a syringe is shown by the details on the notifier when secured with the syringe and allowing usage of the syringe to dispense the accurate dosage.

21 Claims, 23 Drawing Sheets

(51) Int. Cl.
*A61M 5/31* (2006.01)
*A61M 5/32* (2006.01)
*A61M 5/28* (2006.01)
*A61J 1/06* (2006.01)
*A61M 5/19* (2006.01)
*A61M 5/20* (2006.01)

(52) U.S. Cl.
CPC .... *A61M 5/31533* (2013.01); *A61M 5/31578* (2013.01); *A61M 5/322* (2013.01); *A61J 1/065* (2013.01); *A61M 5/19* (2013.01); *A61M 5/28* (2013.01); *A61M 5/3205* (2013.01); *A61M 5/3234* (2013.01); *A61M 5/3243* (2013.01); *A61M 2005/2073* (2013.01); *A61M 2005/3125* (2013.01); *A61M 2205/583* (2013.01)

(58) Field of Classification Search
CPC .. A61M 5/50; A61M 5/5086; A61M 5/31511; A61M 5/3129; A61M 5/008; A61M 5/00; A61M 5/31566; A61M 5/284; A61M 5/31596; A61M 5/31533; A61M 5/3121; A61B 50/362; A61B 50/3001; A61B 50/30
See application file for complete search history.

(56) References Cited

U.S. PATENT DOCUMENTS

| | | | | |
|---|---|---|---|---|
| 3,511,239 | A * | 5/1970 | Tuschhoff | A61M 5/284 604/89 |
| 3,604,583 | A | 9/1971 | Linkletter | |
| 3,850,326 | A | 11/1974 | Ryles | |
| 4,227,615 | A | 10/1980 | Flick | |
| 4,646,926 | A | 3/1987 | Agbay | |
| 4,921,277 | A | 5/1990 | McDonough | |
| 5,000,736 | A | 3/1991 | Kaufhold, Jr. | |
| 5,067,948 | A | 11/1991 | Haber et al. | |
| 5,290,261 | A * | 3/1994 | Smith, Jr. | A61M 5/3129 433/49 |
| 5,807,323 | A * | 9/1998 | Kriesel | A61M 5/14526 604/232 |
| 6,364,866 | B1 * | 4/2002 | Furr | A61M 5/1782 141/330 |
| 6,439,276 | B1 * | 8/2002 | Wood | A61M 5/1782 141/27 |
| 7,097,636 | B2 * | 8/2006 | Pessin | A61M 5/326 604/187 |
| 7,635,344 | B2 * | 12/2009 | Tennican | A61J 1/2096 604/88 |
| 8,034,033 | B2 * | 10/2011 | Grinberg | A61M 5/008 604/189 |
| 8,231,567 | B2 | 7/2012 | Tennican et al. | |
| 8,303,548 | B2 * | 11/2012 | Ito | A61M 5/3135 604/164.08 |
| 8,360,114 | B2 * | 1/2013 | Clark | A61J 1/2096 141/27 |
| 10,004,855 | B2 * | 6/2018 | Leibovici | A61M 5/422 |
| 2001/0030271 | A1 * | 10/2001 | Weesner | A61M 5/008 248/316.7 |
| 2002/0068896 | A1 * | 6/2002 | Robinson | A61J 1/2089 604/82 |
| 2006/0178642 | A1 * | 8/2006 | Gillespie | A61M 5/001 604/228 |
| 2009/0093757 | A1 | 4/2009 | Tennican | |
| 2009/0223994 | A1 | 9/2009 | Getz | |
| 2010/0308055 | A1 * | 12/2010 | Sams | A61M 5/3205 220/324 |
| 2012/0232524 | A1 * | 9/2012 | Hyun | A61M 5/3129 604/514 |

FOREIGN PATENT DOCUMENTS

| | | |
|---|---|---|
| WO | WO 2002/011796 A1 | 2/2002 |
| WO | WO 2006/047813 A1 | 5/2006 |

OTHER PUBLICATIONS

Examination Report No. 2, dated May 12, 2017, in Australian Patent Application No. 2014400365.
Examination Report No. 3, dated Jun. 2, 2017, in Australian Patent Application No. 2014400365.
Examination Report No. 4, dated Jul. 11, 2017, in Australian Patent Application No. 2014400365.
Examination Report No. 5, dated Dec. 19, 2017, in Australian Patent Application No. 2014400365.
Examination Report No. 6, dated Feb. 21, 2018, in Australian Patent Application No. 2014400365.
Notice of Acceptance, dated Mar. 7, 2018, in Australian Patent Application No. 2014400365.
Response to Examination Report, dated Apr. 4, 2017, in Australian Patent Application No. 2014400365.
Response to Examination Report, dated May 17, 2017, in Australian Patent Application No. 2014400365.
Response to Examination Report, dated Jul. 4, 2017, in Australian Patent Application No. 2014400365.
Response to Examination Report, dated Nov. 8, 2017, in Australian Patent Application No. 2014400365.
Response to Examination Report, dated Jan. 16, 2018, in Australian Patent Application No. 2014400365.
Response to Examination Report, dated Feb. 28, 2018, in Australian Patent Application No. 2014400365.
International Search Report, dated Mar. 3, 2015, in International Application No. PCT/AU2014/001066.
Search Information Sheet (SIS), dated Mar. 3, 2015, in International Application No. PCT/AU2014/001066.
Office Action, dated May 17, 2018, in Japanese Patent Application No. JP 2017-545988.
Supplementary European Search Report, dated Sep. 25, 2018, in European Patent Application No. 14897055.

* cited by examiner

Step 1

Step 2

Step 3

Step 4

Step 5

SYRINGE

PRIORITY AND CROSS REFERENCE TO RELATED APPLICATIONS

This application is the U.S. National Phase Application under 35 U.S.C. § 371 of International Application No. PCT/AU2014/001066, filed Nov. 21, 2014, designating the U.S. and published in English as WO 2016/004452 A1 on Jan. 14, 2016, which is identified in the Application Data Sheet filed herewith, and which is hereby incorporated by reference in its entirety under 37 C.F.R. § 1.57

FIELD OF THE INVENTION

The present invention relates to a syringe and in particular to a hypodermic needle syringe. However, it will be appreciated that the invention is not limited to this form of syringe but could include other forms such as needleless syringes.

The invention has been developed primarily for use in an emergency situation such as by ambulance officers will be described hereinafter with reference to this application. However, it will be appreciated that the invention is not limited to this particular field of use.

BACKGROUND OF THE INVENTION

At present syringes are used to impart one or more of a range of medicines into a patient to effect a medical treatment. Their use though needs to be accurate.

Throughout this document and the claims the term "medicine" includes therapeutic, pharmaceutical, nutrient or medicinal material but also includes material which is used as physiologically effective agents or treatment agents including stimulants, coagulants etc.

It is important that the correct medicine at the correct dosage is applied. Therefore the syringe is provided with a dosage chamber with detailed graduations so that an accurate measurement can be taken. The dosage chamber usually needs to be filled with a combination of the medicine at a known concentration and a dosage solution for diluting the medicine to the required application concentration. Often this dosage solution is merely purified water or a medical quality saline solution.

Ampoules are generally used as the secure sealed method of providing highly concentrated and accurately concentrated medicines. These ampoules are monitored exactly at the place of manufacture and then accounted for with high degree of security at distribution areas such as hospitals or other medical outlets. This high control is maintained for a number of reasons including:
  a) as a safety issue, due to the possible highly toxic nature of the medicine if incorrectly used,
  b) due to the high value on illegal drug distributions channels for misuse on non-medicinal purposes
  c) but also in order to maintain and monitor efficacy due to expiry dates of the medicines.

One usual method of use of ampoules is a single use ampoule. This could be a glass ampoule having a main body and a thin neck. The ampoule is therefore clearly sealed and able to show no tampering. Therefore there is a clear knowledge of type of medicine, quality, amount and concentration. The ampoule can then be broken by breaking the neck and the hypodermic needle inserted to withdraw the contents. Separate single or multi use ampoules or other containers contain the dosage solution of purified water or a medical quality saline solution or other suitable solution.

The correct amount of dosage solution can be inserted or drawn into the dosage chamber of the syringe.

However it is often necessary for the preparation of syringe with the dosage chamber filled with the required dosage of medicine and at a known concentration and a dosage solution for diluting the medicine to the required application concentration to be undertaken at a time earlier than its use and by someone else other than the treating medic. This could be the assisting ambulance officer or nurse or other paramedic or other qualified medicine dispensary person at a hospital or medical practice.

Delays can occur between the preparation of the syringe of the required medicine at the required dosage and the use of the syringe to administer the medicine. This can result from other treatment being required first or due to the physical situation of treatment that ambulance officers meet when attending accidents or other emergencies such as traffic accidents, industrial accidents, household accidents and medical emergencies. Further there can be the need for multiple treatments requiring multiple syringes of different medicines at different dosages. Still further multiple syringes could be needed as there are multiple patients at the same accident or emergency and being treated by the same treating medic.

Fundamentally though it is essential that the treating medic, whether an ambulance officer, paramedic, doctor or other physician must be fully aware and check the medicine before administering it. This includes checking that a previously prepared syringe containing a volume of a medicine is in fact drawn from an identifiable source and confirm correct medicine for treatment of a given patient at a given time.

It can be seen that where time is consumed in an emergency situation by having to identify a pre-prepared treatment, any delay in administering a treatment could potentially be fatal.

The present invention seeks to provide a syringe, an irremovable attachment to a syringe or an improved method of identification which will overcome or substantially ameliorate at least one or more of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE INVENTION

According to a first aspect of the present invention there is provided a syringe for use with an ampoule and comprising a dosage chamber able to receive an accurate dosage of medicine and the dosage chamber having an opening for dispensing of the accurate dosage of medicine, a plunger locatable within the dosage chamber to effect the dispensing of the accurate dosage of medicine out of the opening of dosage chamber; an identifier attached to the syringe for identifying the accurate dosage of medicine in the dosage chamber.

The identifier can be an attachment to the dosage chamber.

The identifier can be a fixed attachment to the dosage chamber.

The identifier can be integral with the dosage chamber.
The identifier can be an attachment to the plunger.
The identifier can be fixed attachment to the plunger.
The identifier can be integral with the plunger.

The identifier can be formed as a receptacle for receiving a printed information notifier.

Preferably the syringe has the printed information notifier being detachable from the medicine container containing the medicine.

The identifier can be formed as a chamber for receiving the medicine container containing the medicine after dispensing the contents into the dosage chamber.

The identifier can be formed as a chamber for receiving the medicine container in the form of an ampoule that contains the medicine and includes details about the medicine on the ampoule is broken to allow dispensing of the contents into the dosage chamber and retention of the broken ampoule within the chamber.

Preferably the chamber includes a transparent window allowing reading of the details about the medicine on the ampoule.

The syringe can include a security mechanism for retaining the identifier such that the accurate dosage of medicine in the dosage chamber is known.

Preferably the security mechanism is a one way lockable means so as to allow receipt of identifier and locking to prevent removal of the identifier.

Preferably the security mechanism includes an entrapment mechanism of a one way lockable means is a one way ratchet means for locking receptacle for receiving a printed information notifier after insertion of the notifier.

A syringe according to claim 10, wherein the security mechanism includes an entrapment mechanism of a one way retention means of the chamber for receiving in a irremovable manner an ampoule that contained the medicine and includes details about the medicine on the ampoule which after the ampoule is broken to allow dispensing of the contents into the dosage chamber the broken ampoule is retained irremovably in the chamber.

In one particularly preferred form of the invention there is provided a syringe for use with an ampoule and comprising a dosage chamber able to receive an accurate dosage of medicine and the dosage chamber having an opening for dispensing of the accurate dosage of medicine, a plunger locatable within the dosage chamber to effect the dispensing of the accurate dosage of medicine out of the opening of dosage chamber; an identifier attached to the syringe for identifying the accurate dosage of medicine in the dosage chamber, wherein the identifier is an attachment to the dosage chamber formed as a chamber for receiving the medicine container containing the medicine after dispensing the contents into the dosage chamber, wherein the medicine container is in the form of an ampoule that contains the medicine and includes details about the medicine on the ampoule is broken to allow dispensing of the contents into the dosage chamber and retention of the broken ampoule within the chamber.

Preferably the identifier is a fixed attachment to the plunger.

Preferably the identifier is integral with the plunger.

The syringe can have the security mechanism including an entrapment mechanism of a one way retention means of the chamber for receiving in a irremovable manner an ampoule that contained the medicine and includes details about the medicine on the ampoule which after the ampoule is broken to allow dispensing of the contents into the dosage chamber the broken ampoule is retained irremovably in the chamber.

Preferably the identifier is integral with the plunger.

Preferably the identifier is formed to advise the type of solute.

Preferably the identifier is as a receptacle for receiving a printed information notifier.

The invention also provides a method of identifying an accurate dosage of medicine in a dosage chamber of a syringe including the steps of:
  a) Using an accurate dosage from a detailed single dosage medicine in a frangible medicine container to locate the accurate dosage of medicine in the dosage chamber;
  b) identifying the accurate dosage of medicine in the dosage chamber by retaining the medicine container after being used in a receiving chamber on the syringe;
  c) identifying the solute in the dosage chamber by an identifier;
  d) securing the medicine container within the chamber wherein the accurate dosage of medicine in a dosage chamber of a syringe is shown by the details on the single dosage medicine and the identifier on the solute.

Other aspects of the invention are also disclosed.

BRIEF DESCRIPTION OF THE DRAWINGS

Notwithstanding any other forms which may fall within the scope of the present invention, a preferred embodiment/preferred embodiments of the invention will now be described, by way of example only, with reference to the accompanying drawings in which.

DESCRIPTION OF PREFERRED EMBODIMENTS

Figure 1:
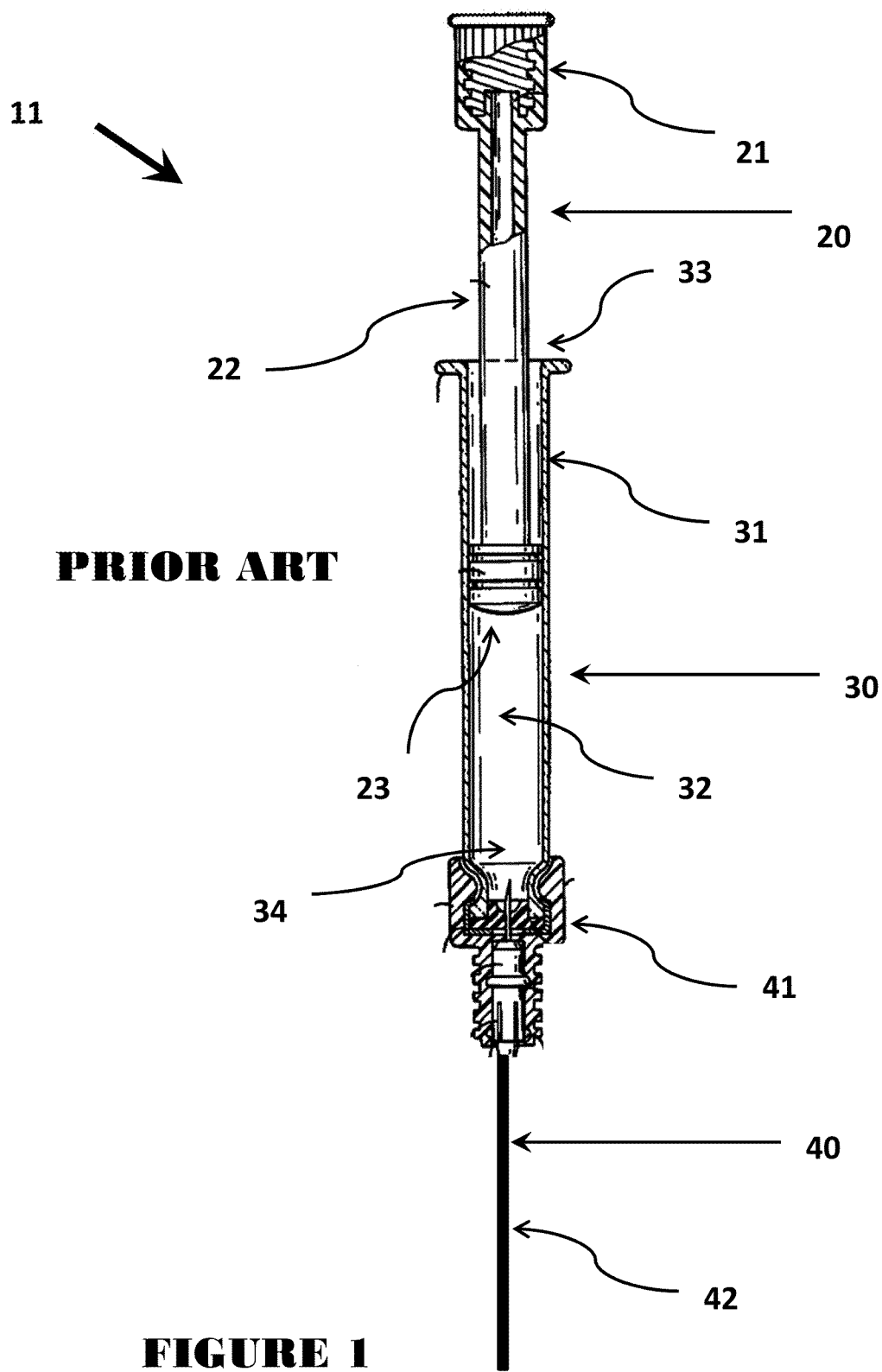
FIGS. 1 and 2 are examples of diagrammatic cross sections of a syringe in accordance with the prior art.

It should be noted in the following description that like or the same reference numerals in different embodiments denote the same or similar features.

Figure 2:
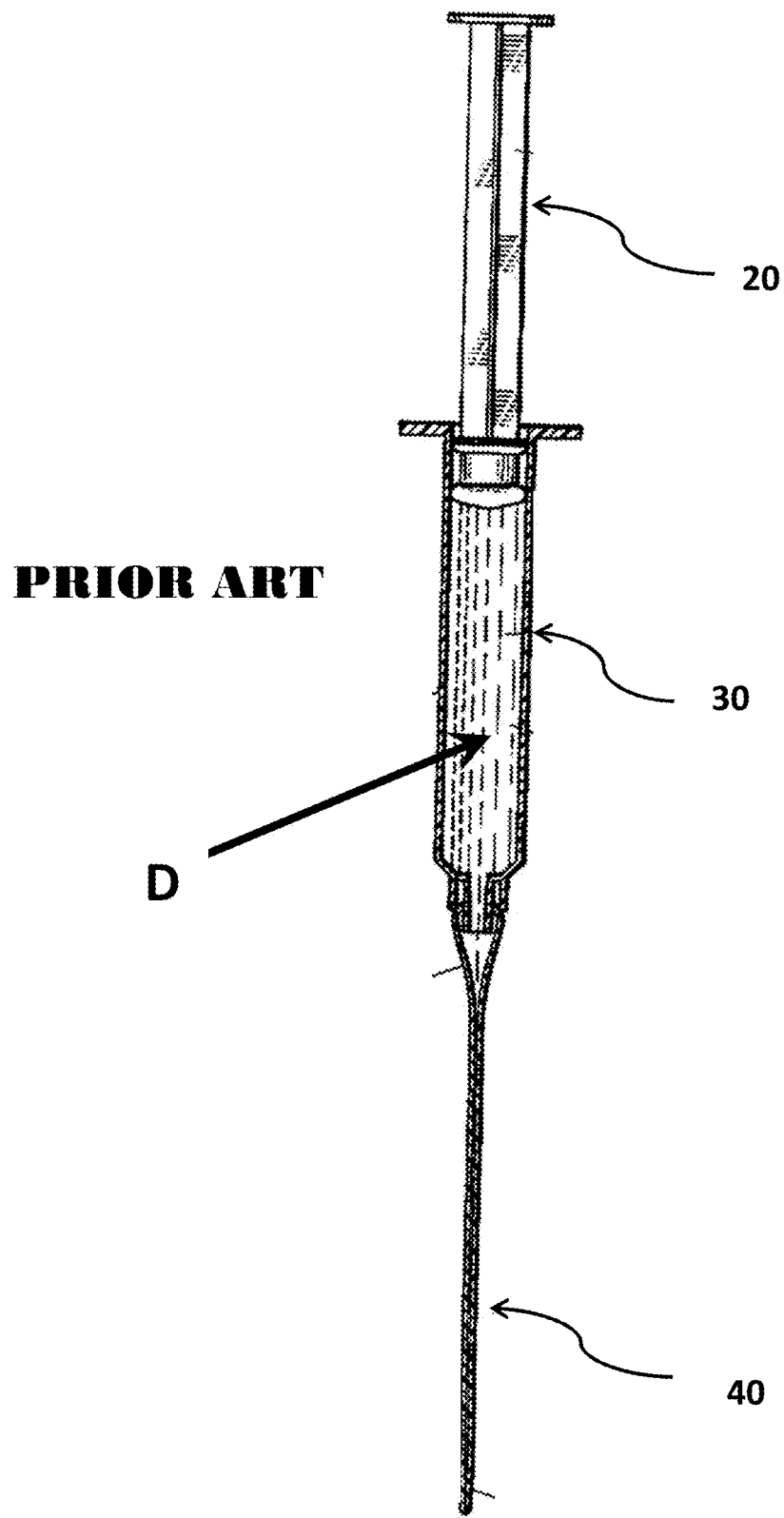

Referring to the drawings and particularly the prior art of FIGS. 1 and 2 there is shown a syringe 11 having a plunger 20 with a finger pushing end 21 and an elongated shaft 22 ending with a O-ring resilient plunger head 23 which is insertable into an open first end 33 of a dosage chamber 30 so as to expel the contents out the other second end 34 of the dosage chamber 30 through a needle arrangement 40.

Generally the dosage chamber 30 is formed by a cylinder 31 with internal cavity 32 extending between open first end 33 and dispensing second end 34. The needle arrangement 40 can include a needle mount 41 attachable to the second end 34 of the cylinder 31 and holding a needle 42 for dispensing subcutaneously into a patient. However the needle arrangement can be other non-needle forms.

Usually the syringe provided with the dosage chamber will receive an accurate dosage D and with detailed graduations an accurate measurement can be taken. The dosage chamber usually needs to be pre-filled with a combination of the medicine at a known concentration and a dosage solution for diluting the medicine to the required application concentration. Often this dosage solution is merely purified water or a medical quality saline solution.

Figure 3:
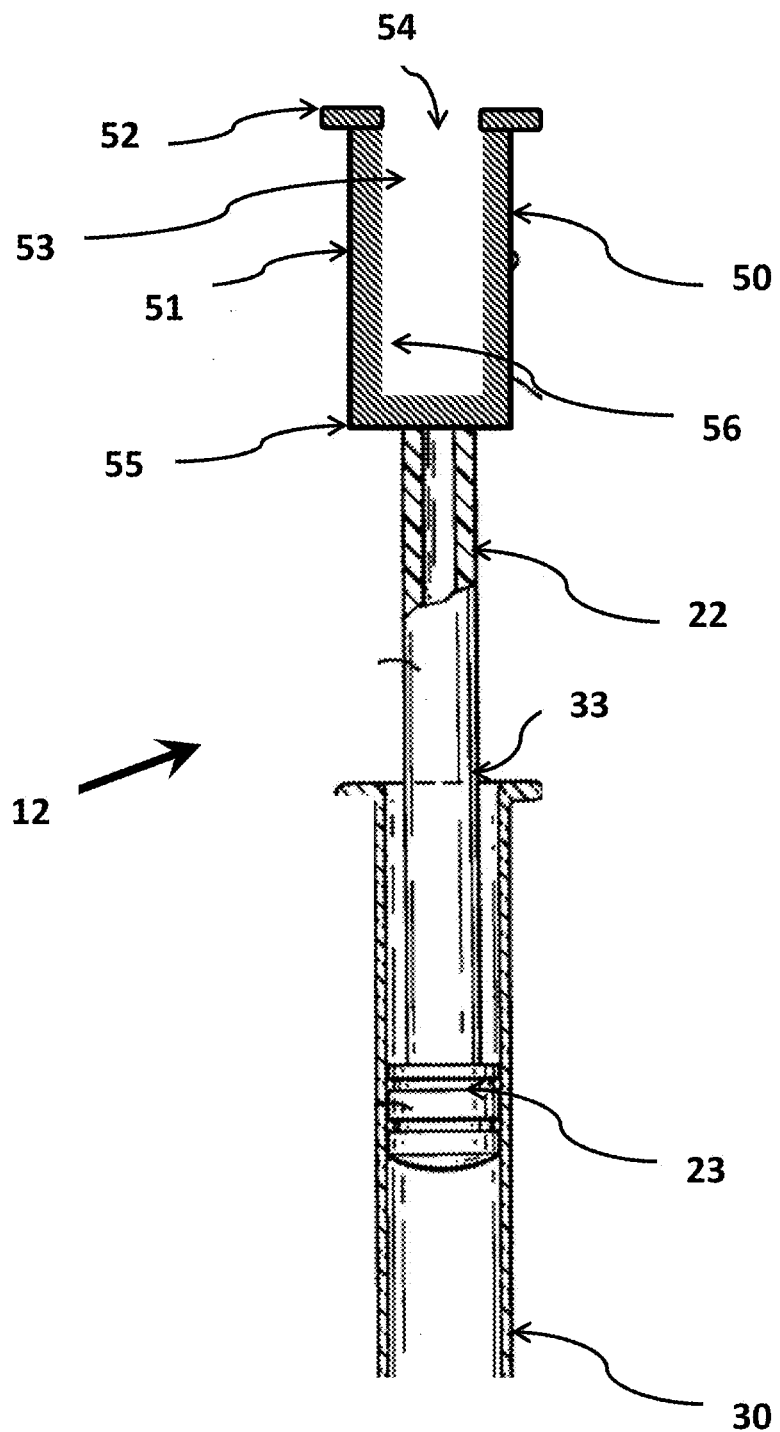
FIG. 3 is a detail of a diagrammatic cross section of a syringe in accordance with a preferred embodiment of the present invention having a chamber integral with a plunger.
Figure 4:
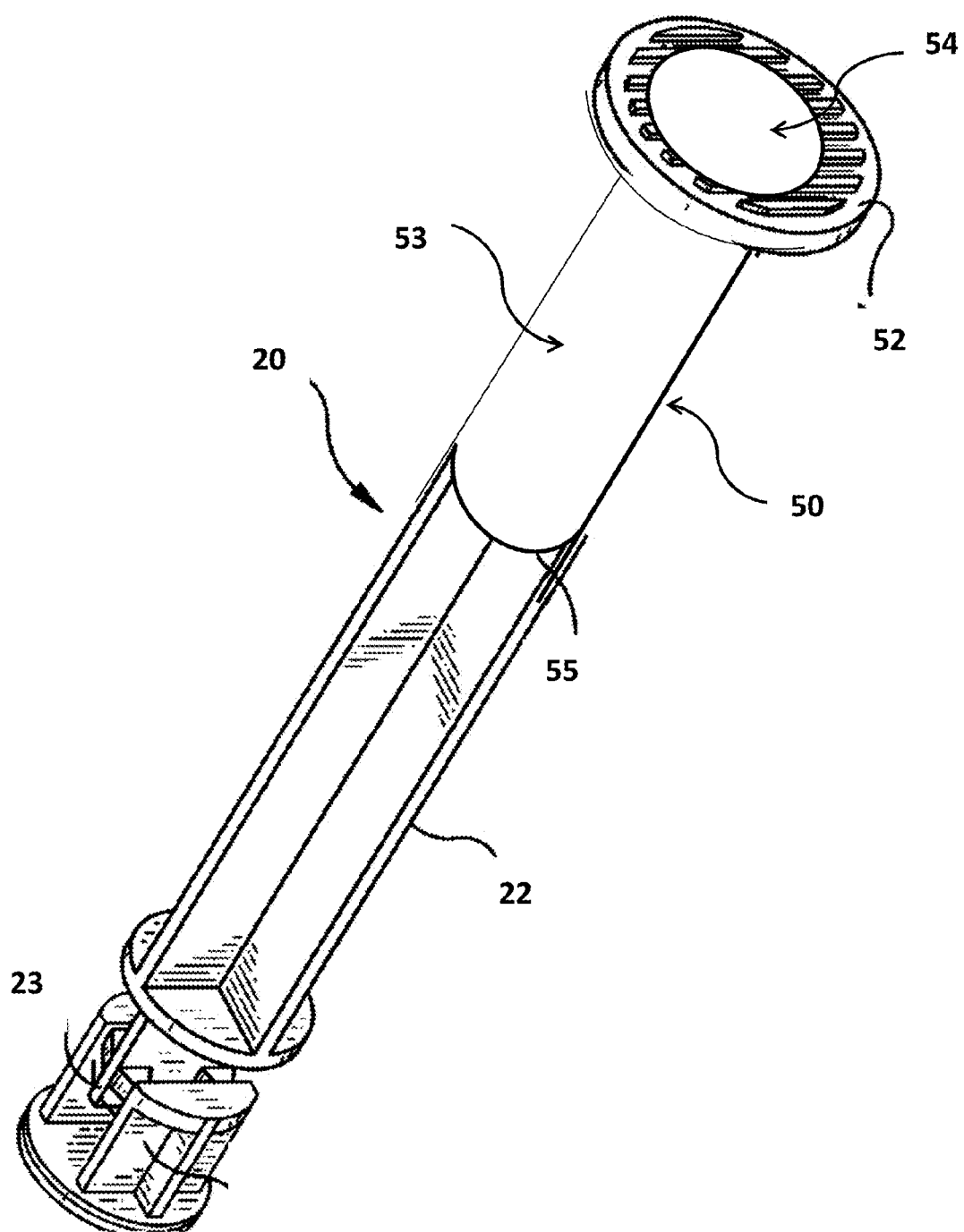
FIG. 4 is a detail of a diagrammatic cross section of a plunger of a syringe in accordance with a preferred embodiment of the present invention having a chamber integral with the plunger.
Figure 5:
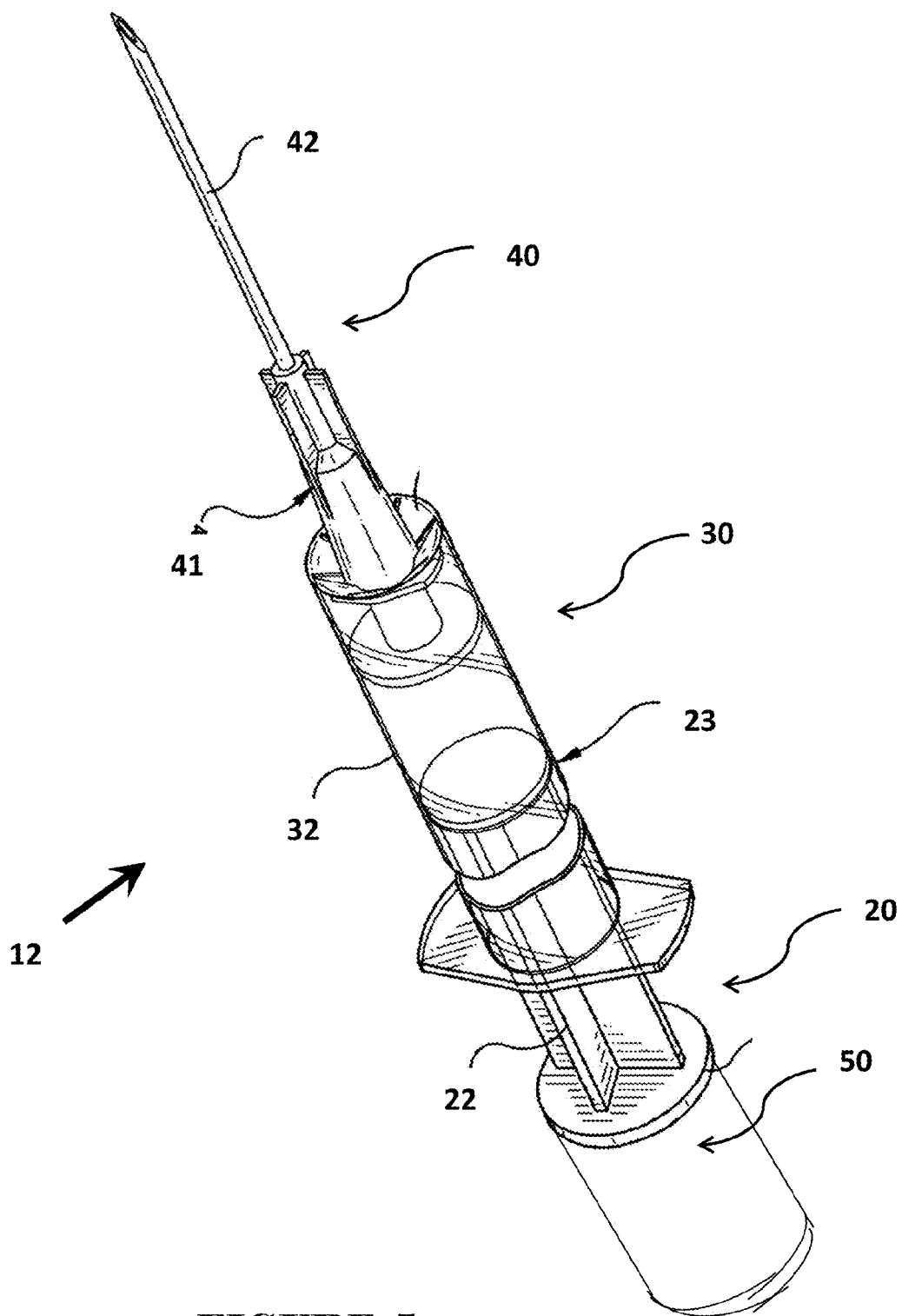
FIG. 5 is a diagrammatic cross section of a syringe in accordance with a preferred embodiment of the present invention having a chamber integral with a plunger.

Referring to the drawings of the embodiments of the invention and particularly the FIGS. 3 to 5 there is shown a syringe 12 for use with an ampoule 45. The syringe has a hollow cylindrical tube forming a dosage chamber 30 able to receive an accurate dosage D of medicine. The dosage chamber 30 has an opening 34 for dispensing of the accurate dosage of medicine such as through a needle arrangement 40 including a needle mount 41 holding and feeding to a needle 42 for dispensing subcutaneously into a patient. A plunger 20 is locatable and insertable into opening 33 at the other end of the dosage chamber 30 to effect the dispensing of the accurate dosage of medicine out of the opening of dosage chamber by being plunged further into the dosage chamber 30.

Of particular importance is the inclusion of an identifier 50 attached to the syringe for identifying the accurate dosage of medicine in the dosage chamber. The identifier can be attached to or a modification of the plunger 20 or attached to or a modification of the dosage chamber 30 or be integral within the plunger 20 or the dosage chamber 30

The identifier in the embodiments shown in FIGS. 3 to 5 is an attachment to the plunger 20 formed as a cylindrical chamber 51 mounted or affixed to the end of the shaft 22 of the plunger 20 to form a modified finger pushing end. The cylindrical chamber 51 of the identifier 50 formed on the end of the plunger has a an opening 54 at one end within an annular finger plate 52 extending perpendicular to the extension of the shaft 22 and central cavity 53 open at the top end by the opening 54 and closed at the other end 55.

The central cavity is sized to receive the used ampoule 45. As shown in one form it could be larger than the diameter of the shaft 22, or equal size to the diameter of the shaft 22 or smaller than the diameter of the shaft 22. The cylindrical chamber 51 is transparent.

The cylindrical chamber 51 is for receiving the medicine container containing the medicine after dispensing the contents into the dosage chamber. The medicine container is in the form of an ampoule 45 that contains the medicine and includes details about the medicine on a non-removable identification badge 48.

The ampoule 45 is usually glass and has a nipple 47 which is broken to allow dispensing of the accurate single dosage contents into the dosage chamber 30. The identifier 50 has the broken ampoule 45 retained within the chamber 53. The ampoule badge 47 includes details about the medicine which after the ampoule is broken to allow dispensing of the contents into the dosage chamber the broken ampoule is retained in the chamber. Therefore the exact details of the medicine are always known even if the syringe is not used immediately but for example 5 to 30 minutes later during attendance at an emergency.

As the identifier 50 is a fixed attachment to the plunger 20 it remains attached to the syringe 12. However the usual operation of the syringe can occur in that the end plate 52 of the identifier chamber 50 can still be used as a finger plate for pushing the plunger 20 when requiring dispensing of the accurate dosage. Preferably the broken ampoule 45 is inserted into the opening 54 of the cylinder 53 with broken nipple 47 leading first into the cylinder so as to keep any sharp edges fully enclosed and away from user. The cylindrical chamber 51 is transparent so that the ampoule badge 47 including details about the medicine is clearly visible.

The syringe further has a security mechanism including an entrapment mechanism 56 on the inner surface of the This entrapment mechanism 56 is a one way retention means of the chamber for receiving in an irremovable manner the ampoule 45 that contained the medicine and which includes details about the medicine on the ampoule. Thereby, after the ampoule 45 is broken to allow dispensing of the contents into the dosage chamber 30 the broken ampoule is retained irremovably in the chamber.

The identifier can also advise the type of solute. The identifier can be a receptacle for receiving a printed information notifier which indicates the solute. A second part of the notifier can provide indication of concentration of dosage due to the addition of the solute.

However the identifier can have other forms such as a break-off tag so that the remaining tag indicates the solute. A second grouping of break off tags can provide indication of concentration of dosage due to the addition of the solute.

In use it can be seen that there is provided a method of identifying an accurate dosage of medicine in a dosage chamber of a syringe. Firstly there is provided an accurate dosage from a detailed single dosage medicine in a frangible medicine container to locate the accurate dosage of medicine in the dosage chamber. Secondly there is identifying the accurate dosage of medicine in the dosage chamber by retaining the medicine container after being used in a receiving chamber on the syringe. Also there is identifying the solute in the dosage chamber by an identifier. In order to ensure there is no tampering or relabeling then there is securing of the medicine container within the chamber.

By these steps it is possible to know without a doubt the accurate dosage of medicine in a dosage chamber of a syringe is shown by the details on the single dosage medicine and the identifier on the solute.

It can be understood that the invention can include variations other than those disclosed in the drawings.

For example a syringe could have the identifier as an attachment to the dosage chamber 30. This could be a cylindrical chamber like the cylindrical chamber 51 which has an integral C-clamp that clamps around the cylindrical dosage chamber.

This C-clamp can include a locking means to prevent removal from the dosage chamber.

The identifier could be a cylindrical chamber like the cylindrical chamber 51 which is a fixed attachment to the dosage chamber.

The identifier could be a cylindrical chamber like the cylindrical chamber 51 which is integral with the dosage chamber.

The identifier could be a cylindrical chamber like the cylindrical chamber 51 which is an attachment to the plunger. As the shaft of the plunger can be a range of shapes from cylindrical to cross shape to x-shape and other cross sectional shapes then the cylindrical chamber 51 can have an integral clamp which affixes to that shape.

The identifier could be a fixed attachment to the plunger or lockable attachment or integral with the plunger. The attachment can be at the end of the plunger such as in FIGS. 3 to 5 so as not to limit the extent of the plunger into dosage chamber 30 or take a small portion of the path of the plunger.

The identifier can be formed as a receptacle for receiving a printed information notifier.

General Characteristics

It can be seen that the invention approaches a number of general characteristics which are new and inventive at least in combination including:
a) Identifier of drug
b) Controlled holder of broken ampoule
c) Notifier of solute
d) Tamperproof
e) Unrestricted use of syringe
f) retrofitting The embodiments of the invention can include one or a combination of more than one of the above features in a synergistic and improved combination that provides an improved and useful development of the art.

a) Identifier of Drug

The drug needs to be clearly identified in any usage. This is important in order to determine what is the material that is being injected which might occur at a later time that when the syringe is initially filled. This particularly occurs when treatment is being performed in an emergency situation because the medical attendee could be undertaking a number of tests and procedures which need to be arranged for prearranged at any critical incident. However the drug also there is to be well-known went in a preplanned approach such as a predefined medical procedure in hospital conditions in which the application of the drug can be initially prepared ready for the time in the preplanned procedure is to be applied.

A particular importance of this identification of drug is already instilled in the supply of the drug by use of ampoules are clearly identified the drug, the source of the drug, the concentration of the drug, the creation date or use by date of the drug, and even the batch number of the drug. Therefore everything from the constituencies of the drug to the possible manufacturing error that may have occurred in a particular batch can be readily identified.

It is clearly useful to maintain the full range of this knowledge and particularly the identification of the drug and concentration of drug by making use of the ampoule itself as the identifier of the drug even after the ampoule has been emptied into the applying syringe. It is therefore an important element to retain the used ampoule with the syringe.

However mere location is not sufficient as it is important that there is no accidental mismatch of the used ampoule and the applying syringe. An even further element of importance is that the information that the ample is providing needs to be readily accessible even after it being used but is being retained with the syringe. In this regard there is a particular requirements of:
 i) tamperproof retention of the ampoule and
 ii) visible the reading of the detailed information on the ampoule lending retained in tamperproof manner to the syringe.
b) Controlled Holder of Broken Ampoule The used drug ampoule needs to be retained with the syringe. Generally ampoules are formed of glass as that is the least reacted to the drug and the most readily decontaminated before filling with the drug. Therefore the next of the ample is shattered in order to open such a small quantity container and such shattered container needs to be retained in a safe manner.

The retention of the ampoule can be by protruding clip on arms that readily hold the ampoule. However such is not an effective means of protecting the user of the syringe from being injured by the protruding shattered ampoule. Further it is not an effective means of allowing ready viewing of the information on the ampoule as the holding arms will cover substantial portion and will hold the ampoule in a single relative position.

Therefore preferably the invention includes a container which is able to receive the shattered ampoule and retain in a safe and enclosed manner. Further by at least a portion of the container being transparent the medical user of the syringe can readily view the substantial information that is available on the extremities of the used ampoule.

It is a substantial advantage of the invention that this container is readily associated with the syringe. This can be achieved by the container being:
 i) attachable to the body of the syringe
 ii) attachable to the plunger of the syringe
 iii) integral with the body of the syringe or
 iv) integral with the plunger of the syringe By the chamber being attachable to the body or plunger of the syringe, it is able to be retrofitted to a syringe. However to increase the security of the relationship between the ampoule and the syringe is beneficial that the connection of the chamber to the body or plunger of the syringe is not reversible seven of the chamber cannot be accidentally detached and re-attached to one of a multiple number of possible syringes.

However a significant benefit is achieved by the chamber being integral with the body or plunger of the syringe. In this way there is no action required in order to associate the chamber with the syringe as it is already fully associated and cannot be misunderstood as being associated with that syringe. Still further the integral element of the chamber with the body will plunge of the syringe increases the effective use of correct procedure in retaining the substantial information on the broken ampoule after the drug has been inserted into the syringe, as it is readily available and already in the hands of the medical user or person preparing the syringe for the medical user.

To further add benefits to the correct association of the used ampoule to the syringe into which the drug from the ampoule has been inserted, the chamber can include a tamperproof closure. Therefore after the used ampoule is inserted into the chamber, the tamperproof closure can permanently retain the ampoule in the chamber.

The chamber can be integral with the body of the syringe by being:
  i) in line with the syringe and line of insertion of the plunger into the syringe or
  ii) otherwise attached or adjacent to but in an integral manner to that direct in line position.

This can mean that the chamber takes a portion of the dosage chamber of the body the syringe and can move within the dosage chamber upon pressure from the plunger. However if the chamber is not in line with the syringe and the line of insertion of the plunger you can remain in a fixed integral position adjacent the dosage chamber and still be readily accessible and associated with the syringe. The volume of the dosage chamber will not be affected by the chamber holding the used ampoule.

Similarly the chamber can be integral with the plunger of the syringe by being:
  i) in line with the linear insertion portion of the plunger into the syringe or
  ii) otherwise attached or adjacent to but in an integral manner to that linear position.

With the chamber in line with the plunger, it can have a structural integrity such that it forms part of the plunger duties and is inserted into the dosage chamber of the syringe in order to expel the dosage of drug from the other end of the dosage chamber. In this way the chamber has a dimension limited to the internal dimension of the dosage chamber. It can be seen that the chamber the holding used ampoule could still be part of the plunger while not being a portion that needs to proceed insertion into the dosage chamber. In this regard the chamber holding the used ampoule of it forms a rear portion of plunger. Further the chamber in this form can have a direction greater than the dosage chamber and therefore receive and ampoule with dimensional greater than the dosage chamber.

A particular benefit of the chamber not proceeding into the dosage chamber of the syringe is that the details of the ample more readily viewable through a single thickness of the chamber holding the used ampoule rather than needing viewing through both the dosage chamber and the chamber holding the used ampoule.

However it can be seen that this complication can be overcome in that the timing for the need to read the ampoule is prior to the usage and dispensing of the drug from the dosage chamber. Further if it is needed that the details of the drug that has been administered is required then the withdrawal of the chamber from the dosage chamber will allow ready viewing through a single transparent wall of the chamber holding the used ampoule.

Overall therefore the chamber when in line with the plunger can form the entire plunger or only a portion extending from the extreme finger pushing end of the plunger. Further the chamber can be done mentioned smaller, equal to, or greater than the diameter of the dosage chamber.

An important element of the chamber is that it includes a closure that retains the used ampoule therein. Therefore it is preferable that this opening into the chamber and closure thereof is situated at the extreme finger pushing end of the plunger when the chamber is in line with the plunger.

c) Notifier of Solute

The drug that is administered is of importance not only by its identification but also by its concentration. The drug initially is provided at a particular concentration identified by the ampoule. The quantity of the drug that is being administered can be identified by point of the quantity markings along the length of the dosage chamber of the syringe. However the drug may be required to be administered at a different percentage concentration. It is therefore known to have the drug provided in the syringe in a decreased concentration by the inclusion of a drug inert solute. This site had is usually saline or purified water or the like.

It can therefore be seen that it is important to identify solute features of:
  i) the type of solute,
  ii) the amount of solute, and
  iii) the resultant concentration of the drug.

Clearly having two of these pieces of information will provide the third.

It is particularly beneficial in the invention that the steps of identifying the features of the solute are readily achievable by the medical user or the assistant to the medical user. It is possible that this information can be written on the extremity of the syringe or the plunger or the chamber holding the used ampoule. However handwriting is not a clear indicator and writing on an extremity particularly with felt pens or biros or the like can result in smudging of the information so as to make it illegible.

Therefore a particularly important version of the invention includes a solid identification or notification mechanism that incorporates elements of the syringe. This can be the syringe body or plunger having a number of predefined snap off portions of the medical user or assistant can readily choose the appropriate one that identifies one or more of the above identified solute features.

d) Tamperproof

As identified above it is important that the details of the drug that is in a syringe is clearly identifiable including other characteristics such as concentration and alteration of that concentration by means of a solute. Therefore in an emergency situation where an assistant to a medical user has prepared the syringe with the required mixture of drug and solute is necessary for the medical user to be fully assured of the correct information available and the contents of the syringe. If a medical user does not have such confidence they would wish to remix and restart the contents of the contents of the syringe.

Elements of certainty that are provided in the system which provides such confidence to the medical user is the amount of exact information detailed on the used ampoule as well as the notification mechanism of the type and amount of solute.

A further element is added to it even further add confidence to the medical user by having tamperproof closure of the chamber holding the used ampoule. Still further if the chamber is integral with the syringe there can be no question of the accuracy of the information of the contents of the syringe. If the chamber is not integral and it also would be preferable to have a tamperproof mount of the chamber to the body of the syringe or the plunger. This again will secure the accuracy of the information of the contents of the syringe.

There are a number of ways of obtaining such tamperproof connection including one way insertion of sawtooth protrusions into a receiving socket. Another wave may merely be a sawtooth protruding clip which engages an overhanging rim.

e) Unrestricted Use of Syringe\Needle it is important in the present system to ensure that the substantial benefits of one or more of the characteristics do not affect the use of the syringe and needle. Other characteristics can be combined with such substantial benefits of the present system such as use with retractable or disposable needles. Further it can be used with prefilled dosage chambers.

f) Retrofitting

The approach that has been taken in providing substantial benefits detailed above is preferably included in integral formations and therefore is created at manufacture. However the novel features and design are also included on integral chambers that holds the used ampoules in which such changes are attachable to the syringe body or plunger. This allows the benefits of the invention to be applied retrospectively in a retracted format to pre-manufactured syringes.

Examples of Needles/Syringes

Figure 6:
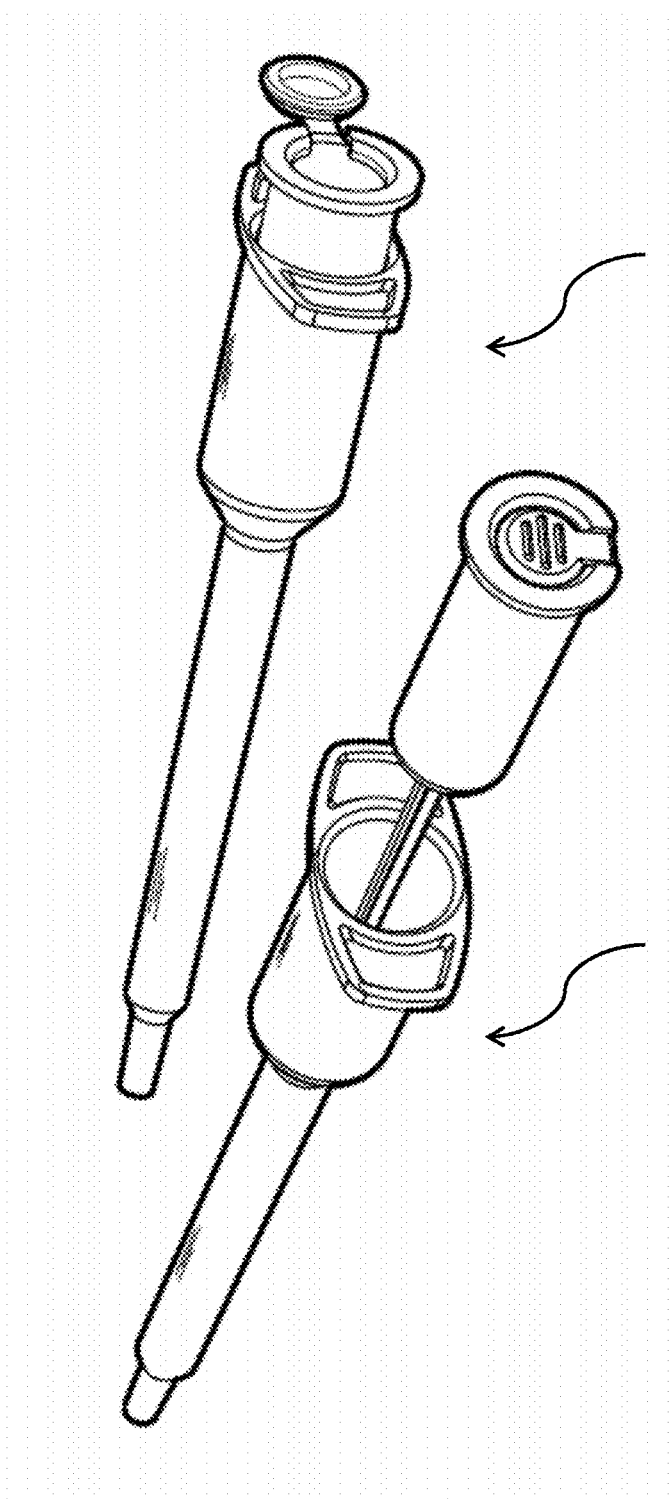
FIG. 6 is a perspective diagrammatic view of two forms of the preferred embodiments of the present invention identified as a large syringe and a small syringe and respected chambers for holding the used ampoules.

In examples of the invention there can be a plurality of different types of needles to which the invention can be applied including as shown in FIG. 6 of:

a) Medium to large volume i.e. greater than 5 ml b) Small volume i.e. less than 5 milliliters (ml)

c) Safety needles including retractable needles d) Other forms including disposable and pre-filled syringes.

Example A—Medium to Large

Figure 7:
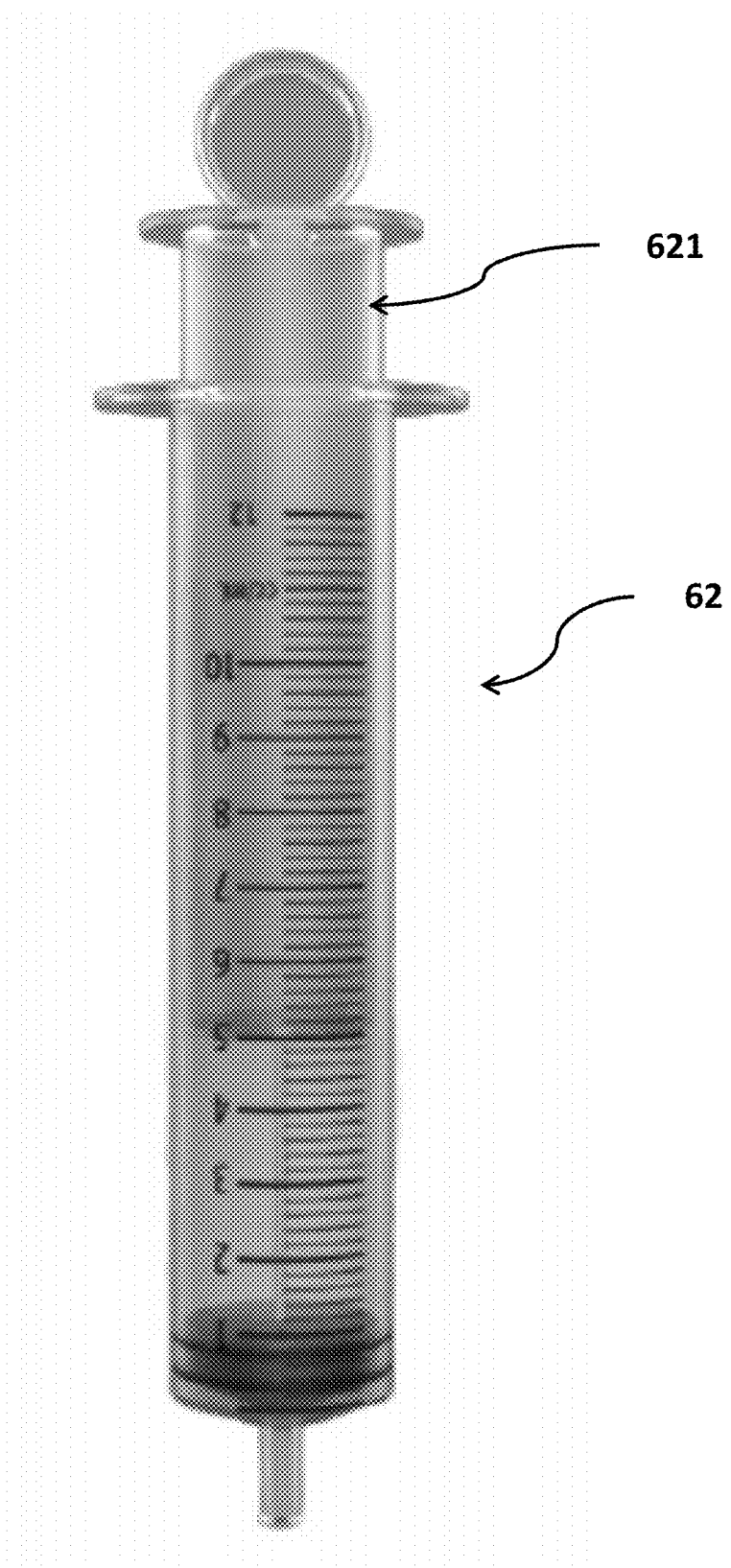
FIGS. 7 and 8A and 8B are diagrammatic views of a large syringe in a combined form and in a separate component form.
Figure 8A:
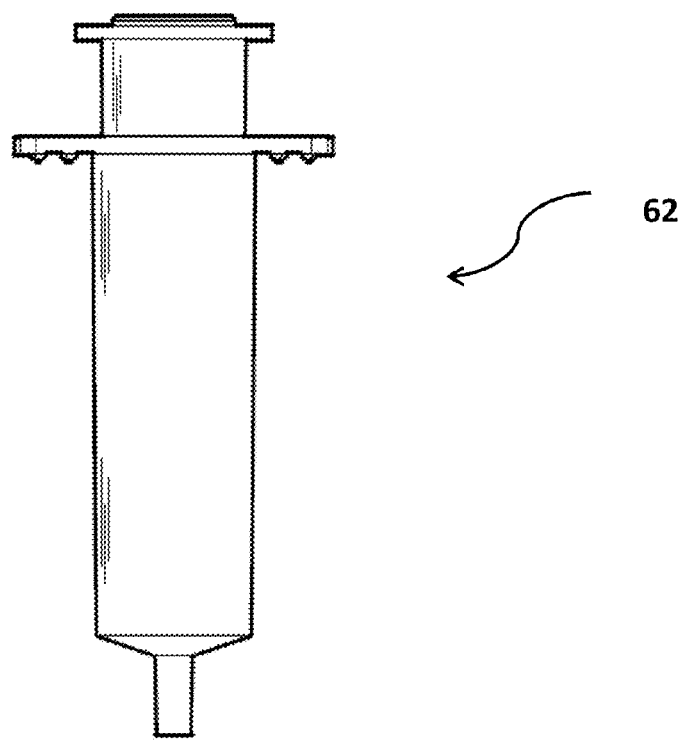
Figure 8B:
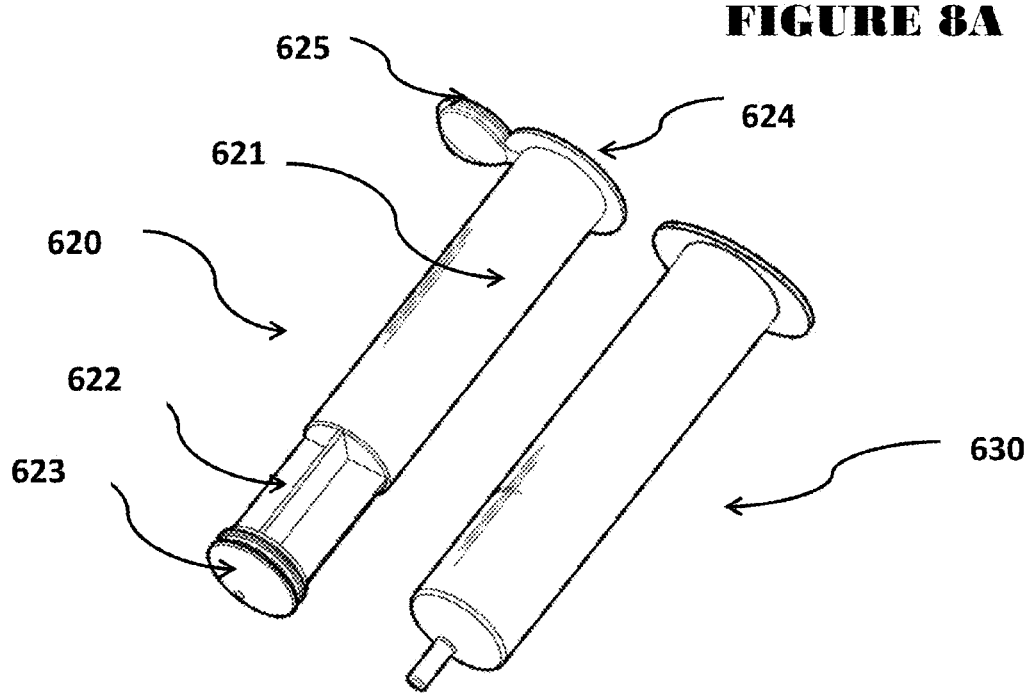
Figure 9:
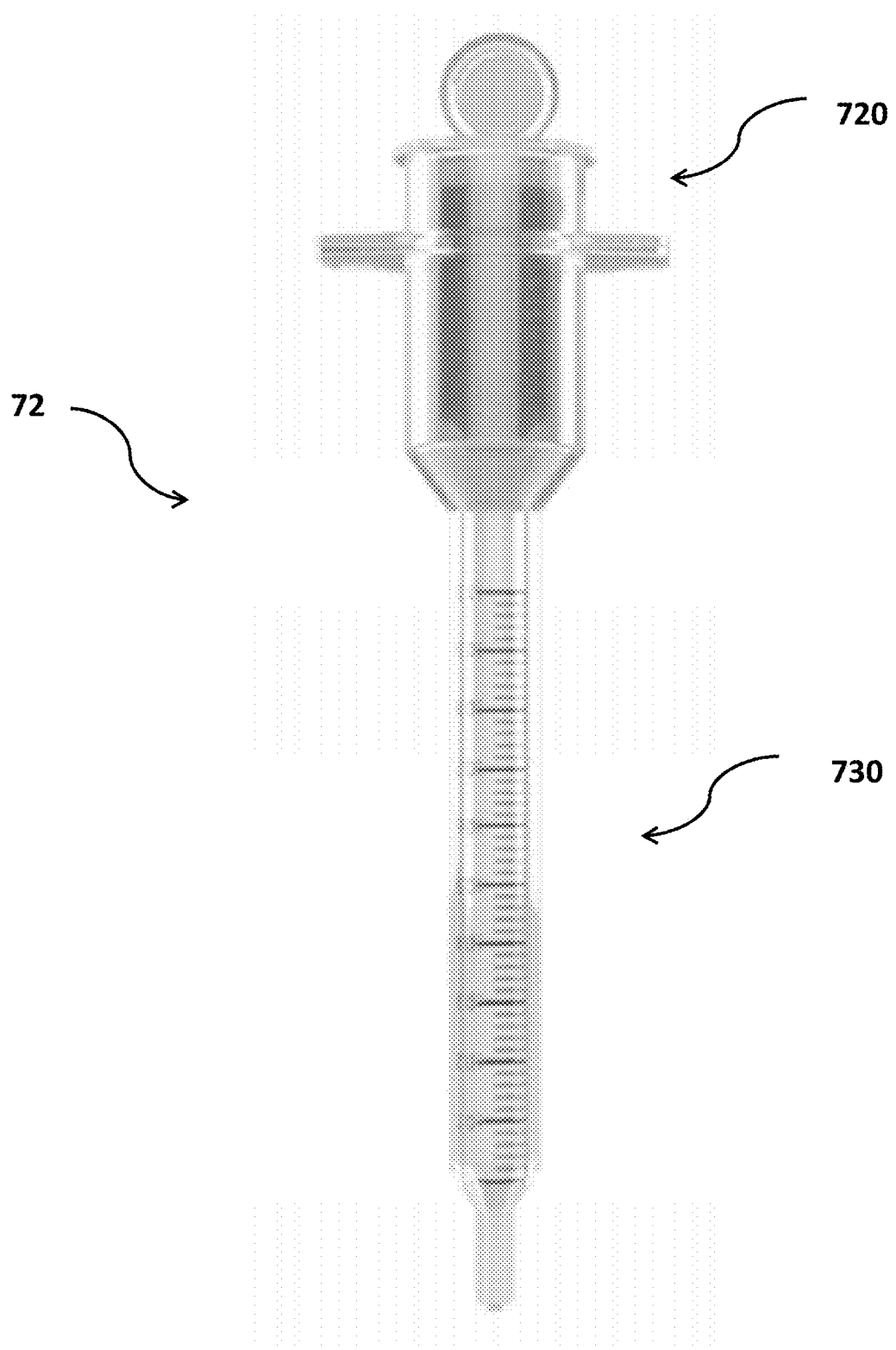
FIGS. 9, 10A, 10B, 11 and 12 are diagrammatic views of a small syringe of FIG. 6 in a combined form and in a separate component form.
Figure 10:
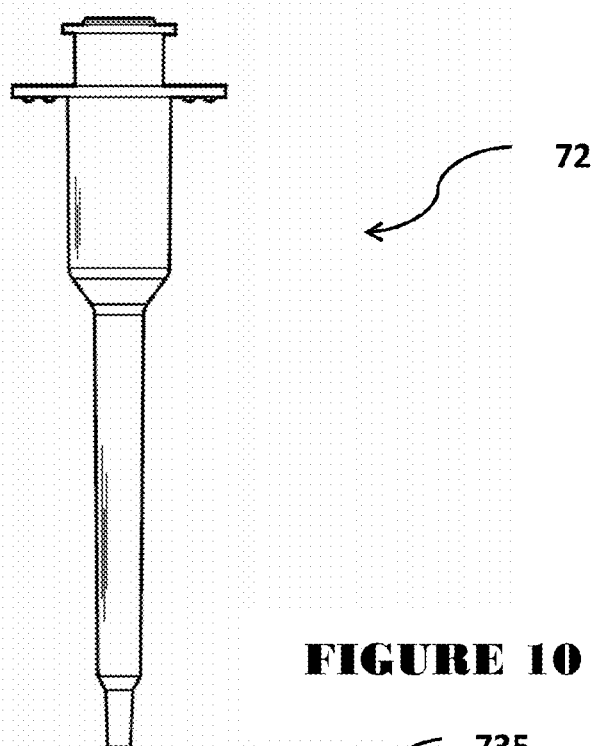
Figure 10:
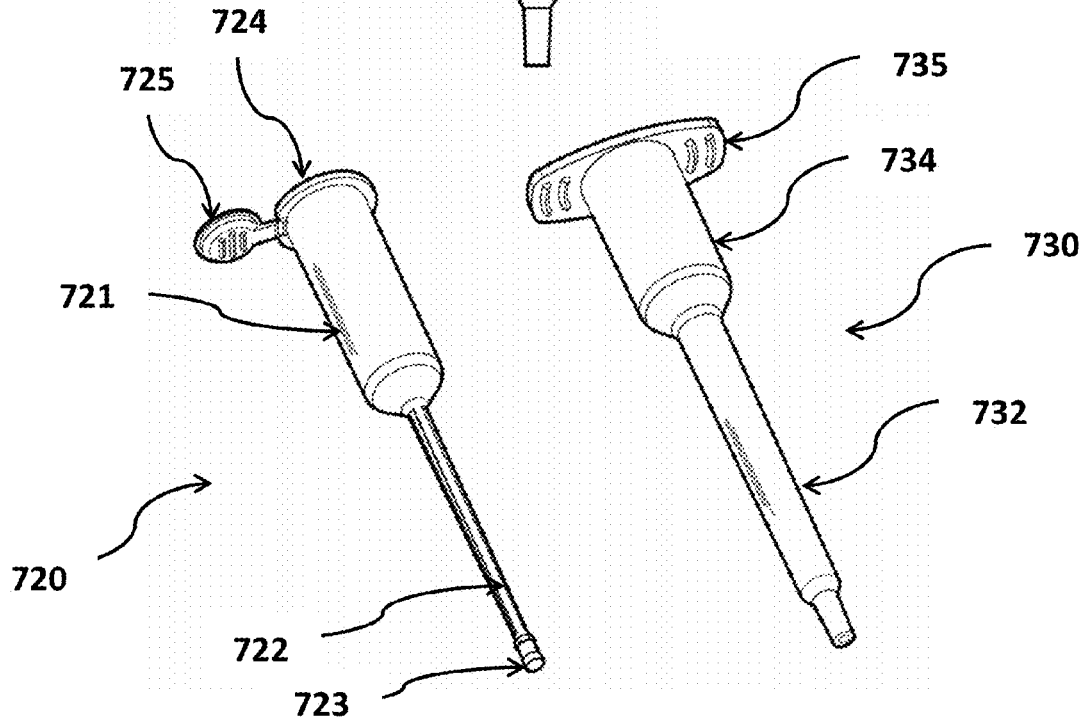
Figure 11:
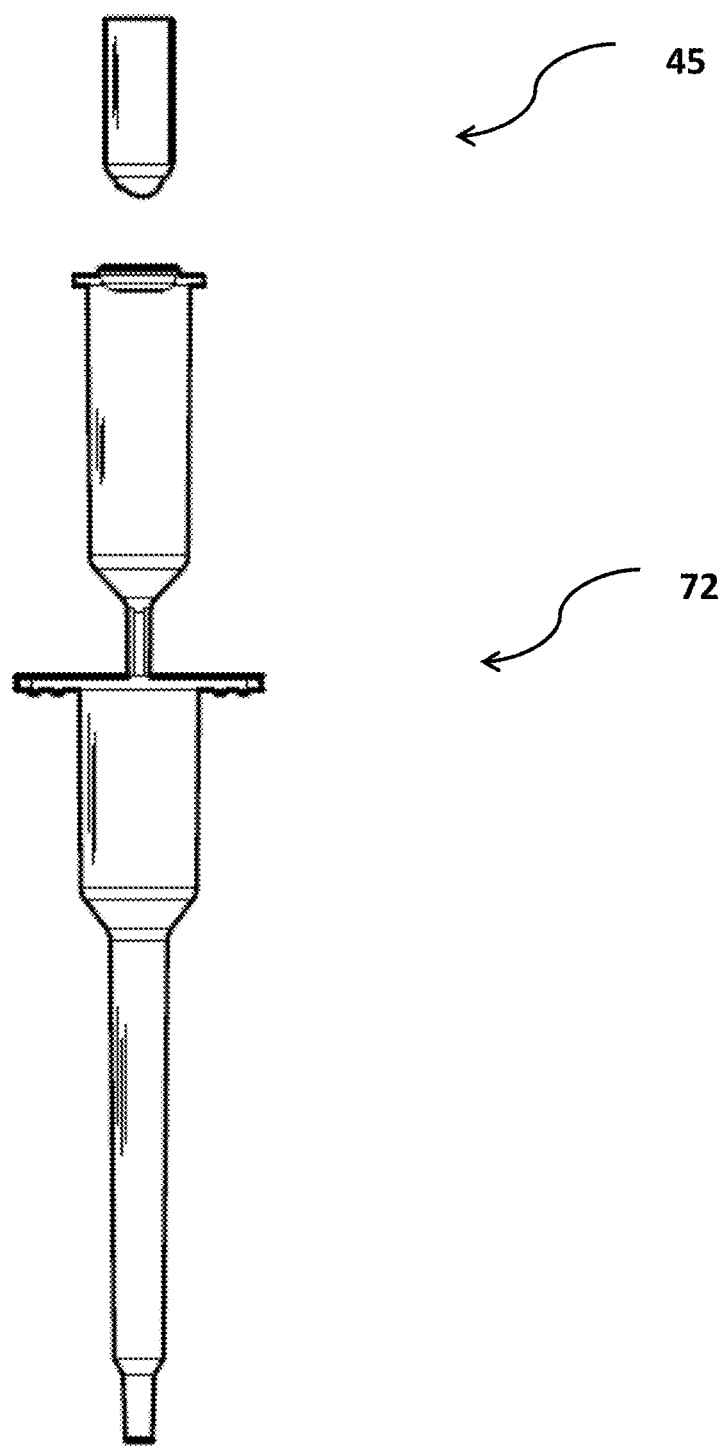
Figure 12:
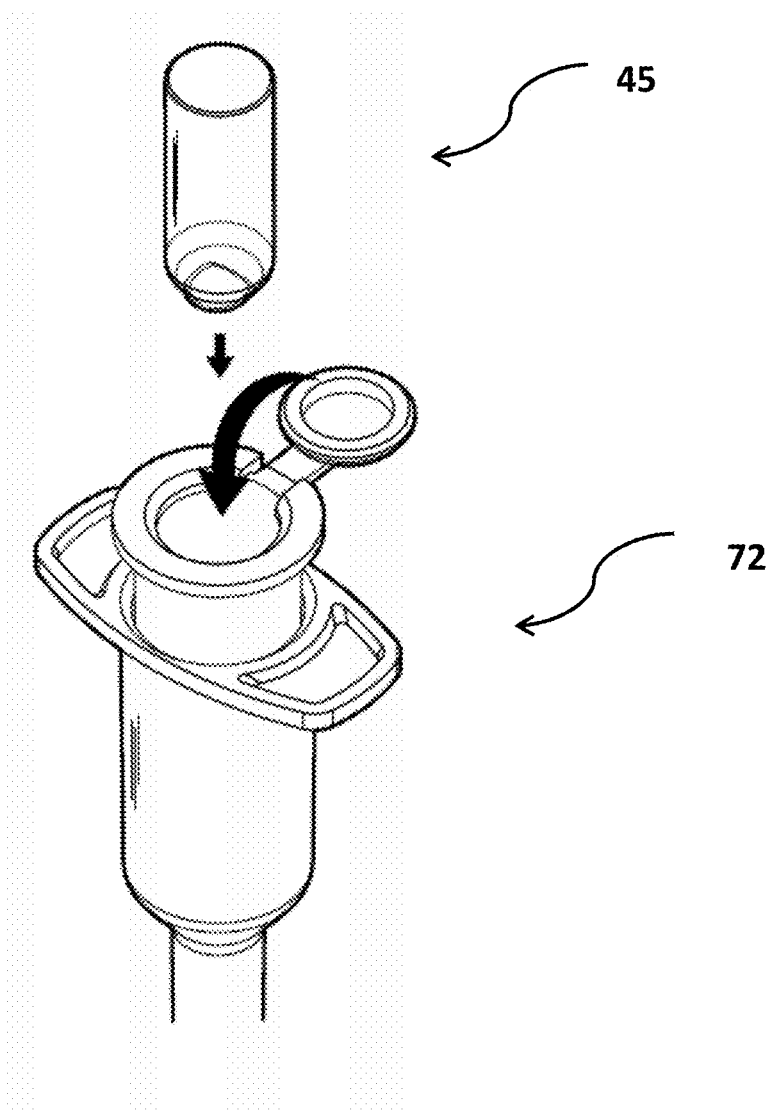
Figure 13:
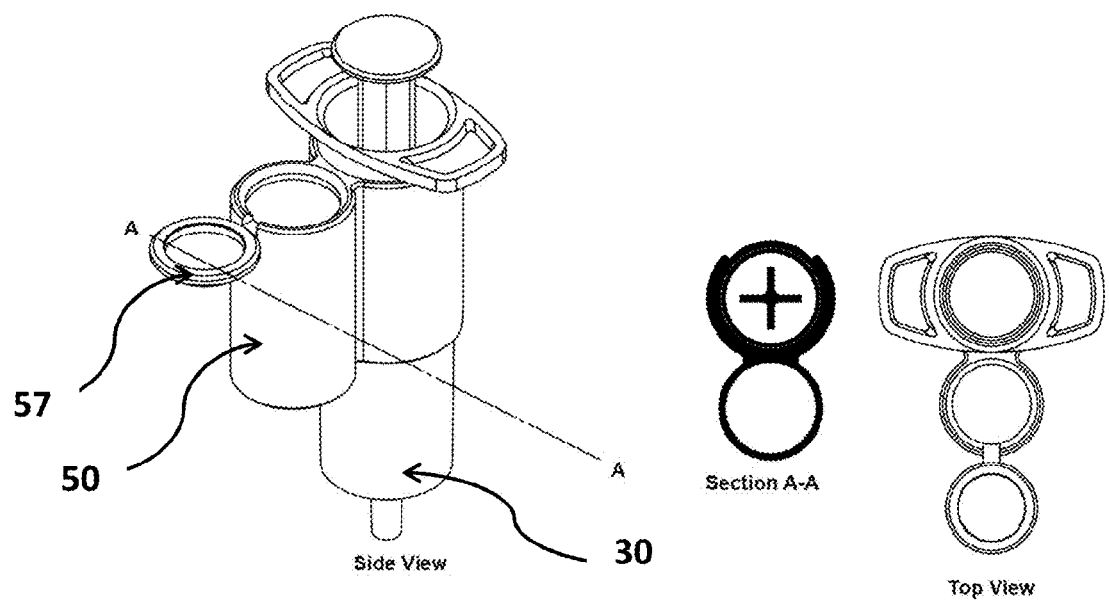
FIG. 13 a diagrammatic views of examples of separate chambers for holding used ampoule in which the chamber can be attached to the syringe body all plunger.
Figure 13:
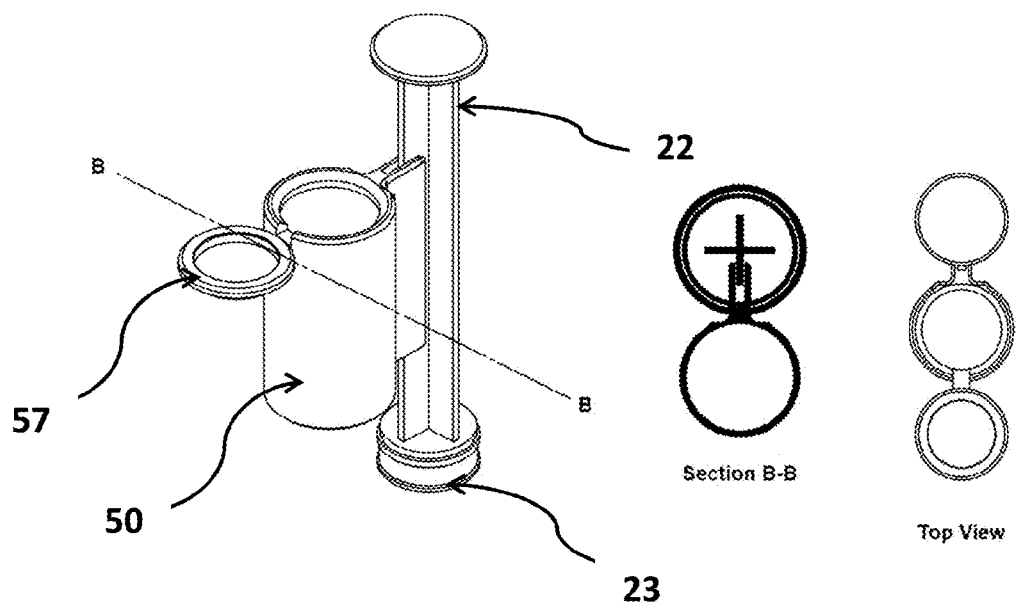
Figure 14A:
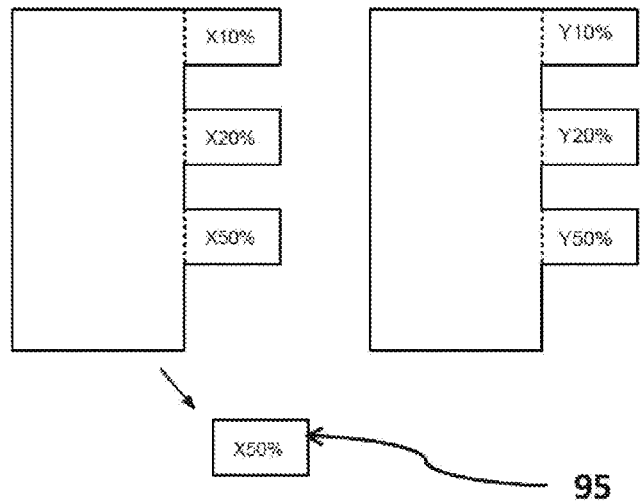
FIG. 14 is a diagrammatic view of examples of notification of the type of solute or volume of solute contained in the dosage chamber of the syringe.
Figure 14B:
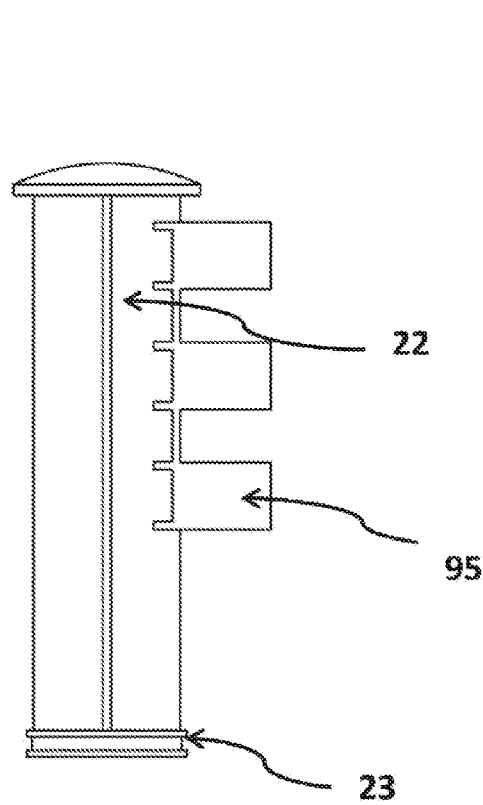
Figure 14C:
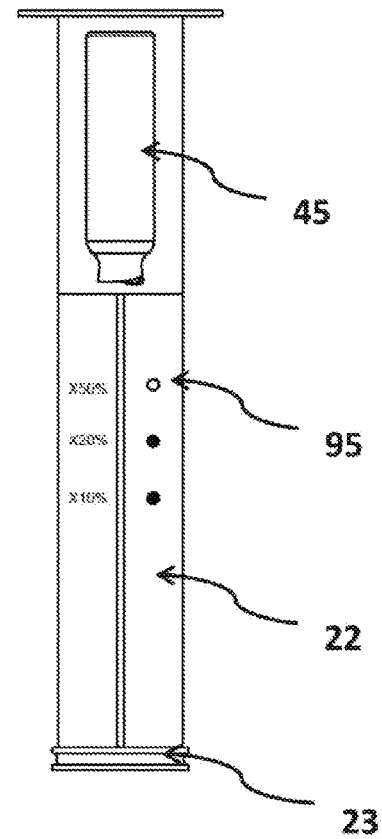
Figure 15:
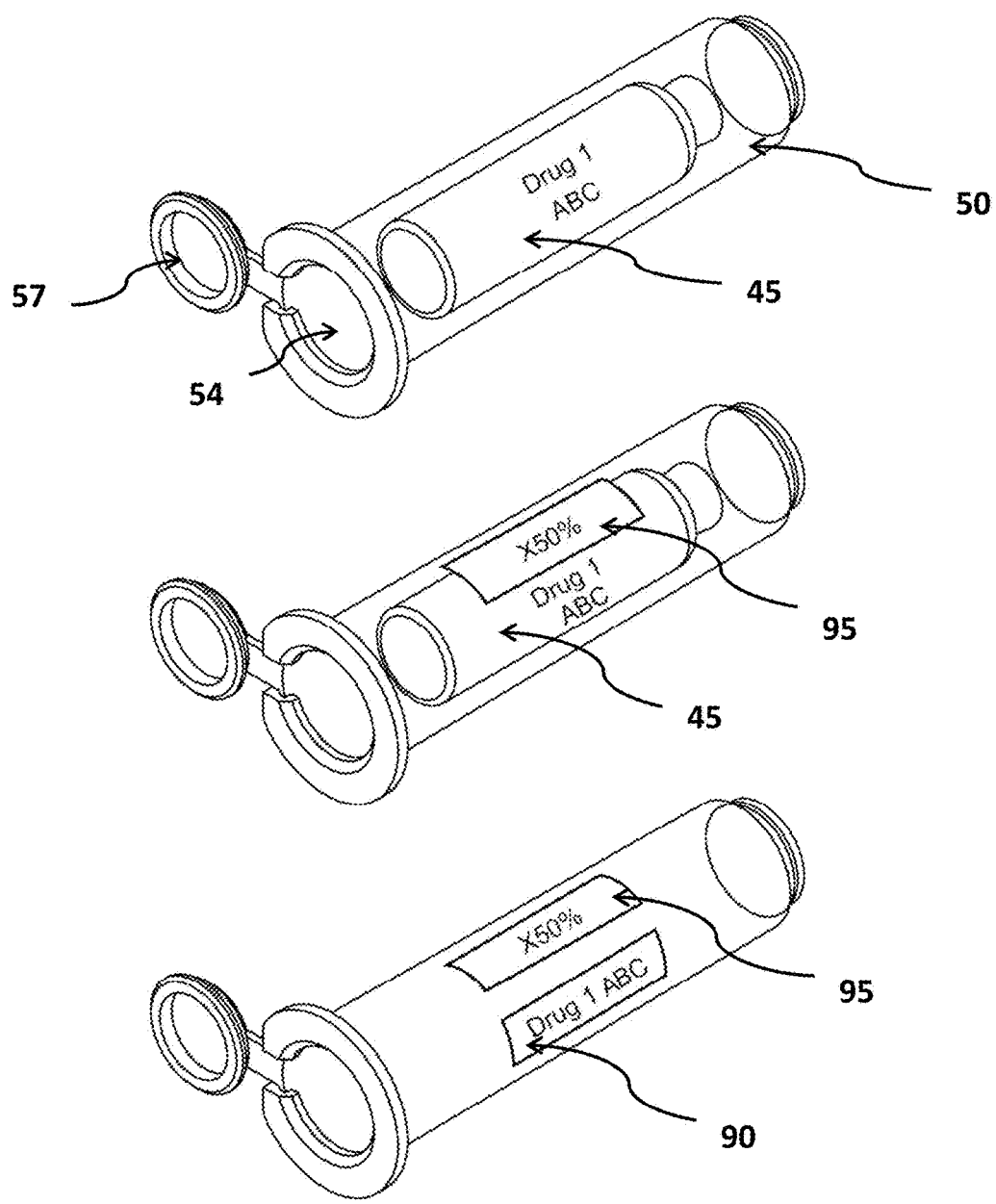
FIG. 15 of diagrammatic view of examples of notification of the resultant concentration of the drug and solute in the dosage chamber of the syringe.

Referring to FIGS. 7, 8A and 8B there is a particular preferred example of a medium to large volume syringe 62. In particular this is a preferred example of a medium to large volume syringe where the chamber to hold the used ampoule is integral with plunger 620 and has a diameter substantially equal to the diameter of the dosage chamber 630 of the syringe.

The identifier in the embodiments shown is an attachment to the plunger 20 formed as a cylindrical chamber 621 mounted integral to one end of the shaft 622 of the plunger 620 to form a modified pushing end and still allow other end 623 to force the contents in the syringe 630.

The cylindrical chamber 621 formed on the end of the plunger 620 has an opening 624 at one end within an annular finger plate extending perpendicular to the extension of the elongation of the plunger 622 and central cavity of the chamber 621 open at the top end by the opening 624 and closable by a hinged lid 625. This lid can be tamperproof closable so that contents cannot be withdrawn. The central cavity is sized to receive the used ampoule 45.

Example B—Small

Referring to FIGS. 9, 10A, 10B, 11 and 12 there is a particular preferred example of a small volume syringe 72 i.e. less than 5 milliliters. In particular this is a preferred example of a small volume syringe 72 where the chamber to hold the used ampoule is integral with plunger 720 and has a diameter substantially greater than the diameter of the dosage chamber 732 of the syringe 72.

The identifier in the embodiments shown is integral to the plunger 720 formed as a cylindrical chamber 721 mounted integral to one end of the narrower shaft 722 of the plunger 720 to form a modified pushing end and still allow other narrower portion 722 and end 723 to force the contents in the dosage chamber 732 syringe 730.

The cylindrical chamber 721 formed on the end of the plunger 720 has an opening 724 at one end with an annular finger plate extending perpendicular to the extension of the elongation of the plunger 722 and central cavity of the chamber 721 open at the top end by the opening 724 and closable by a hinged lid 725. This lid can be tamperproof closable so that contents cannot be withdrawn. The central cavity is sized to receive the used ampoule 45.

Example C—Retractable

Figure 16:
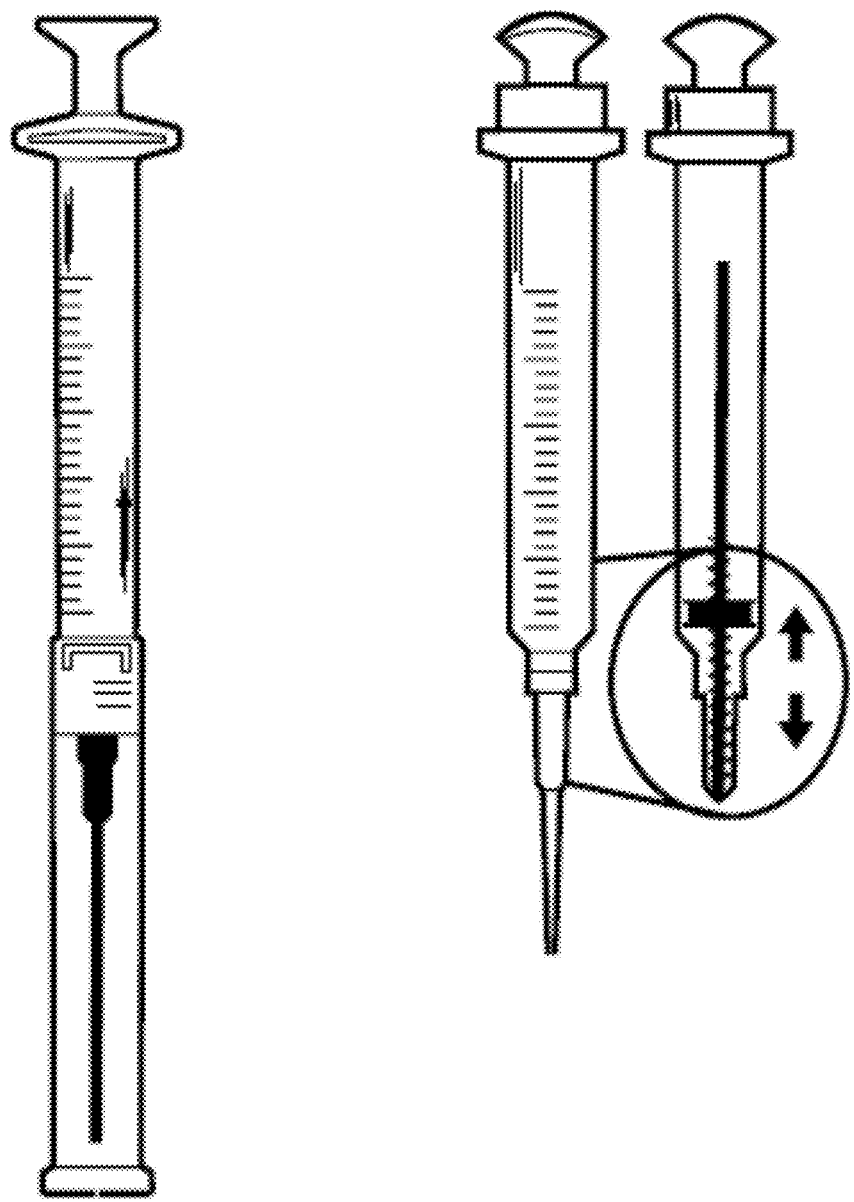
FIGS. 16 and 17 are diagrammatic views of known protected needles of syringes or retractable needles to which the invention can also be applied.
Figure 17:
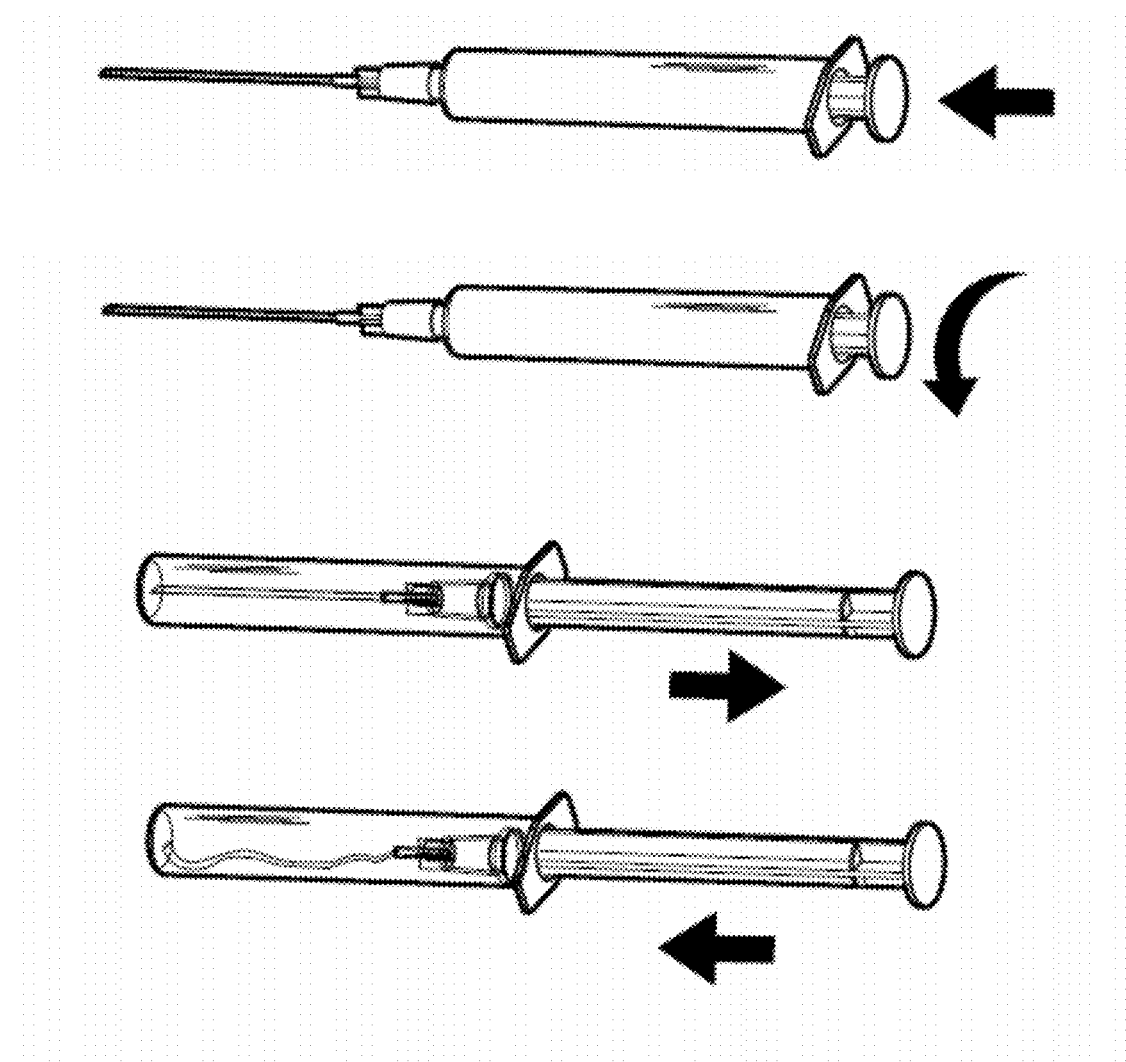
Figure 18:
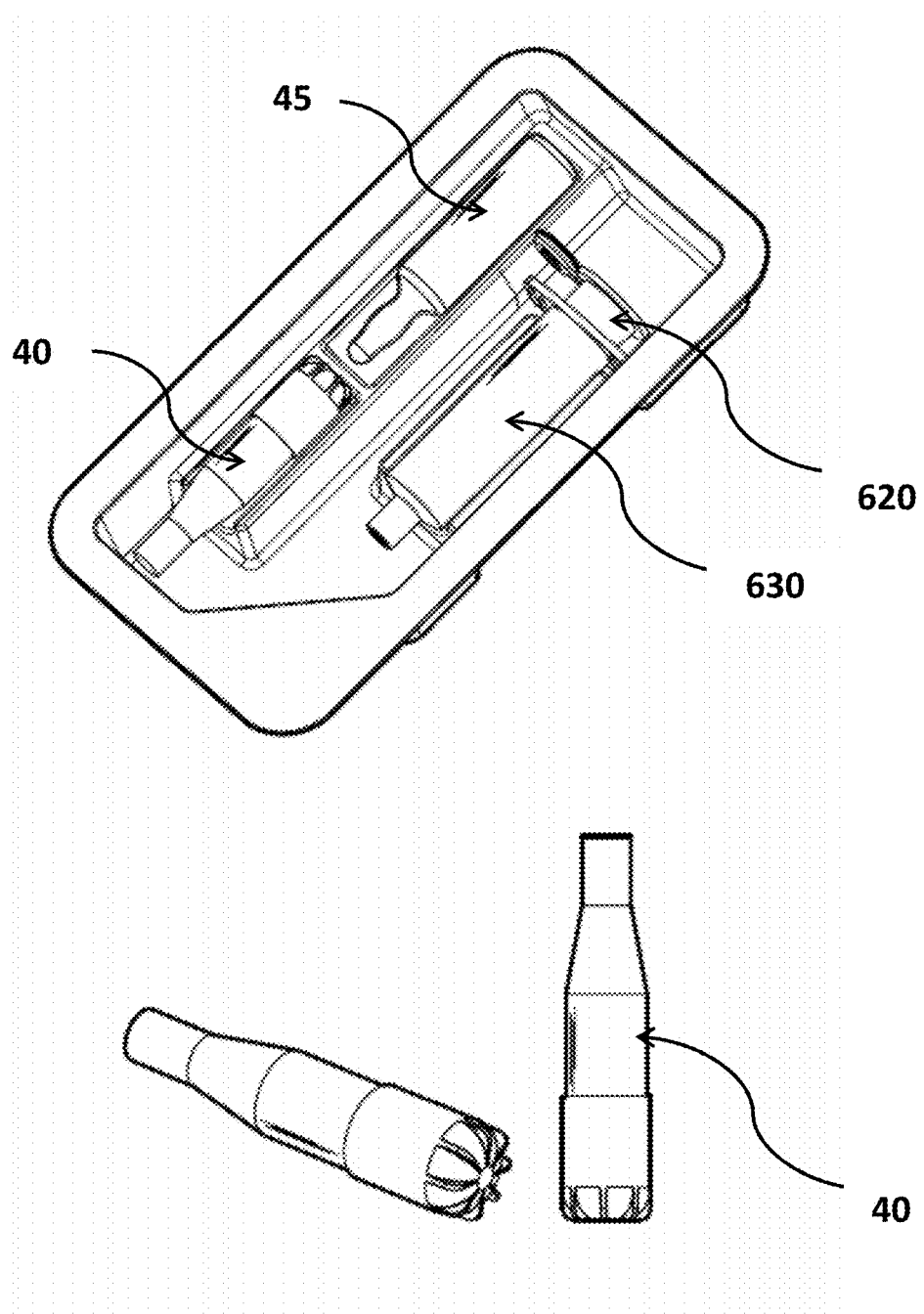
FIG. 18 is a diagrammatic view of known pre-filled syringes to which the invention can also be applied.

Many syringes include retractable needles due to the occupational health and safety concerns and general safety concerns. However such mechanisms, such as the examples shown in FIGS. 16 and 17 can readily be used in combination with the arrangements of the invention.

In one form the mechanism for retraction is a separate clip-on arrangement to the end of the syringe. This has no effect on the syringe and therefore a range of embodiments of the invention can readily be used with such retractable needles.

In another form of retraction mechanism, the needle is protracted from the syringe while in use but retracted into the syringe after use. The invention in some forms can be readily applied to this form of needle. If required and suitable, the dosage chamber could merely be extended so that not only is it able to contain the dosage of drug and solute but also to be sized to retain the syringe after use. Further the dosage chamber could further include a container that holds the notifier that includes details The operation of the plunger can be on the chamber holding the notifier so that it is withdrawn along the dosage chamber to allow room for the needle to be retracted.

However retraction mechanisms are more readily useable with embodiments of the invention in which the chamber holding the notifier is integral with the syringe, or is attached alongside the dosage chamber or syringe. In this way the operation of the retractable needle is not altered from its usual mechanism while gaining the substantial benefits of the invention.

Example D—Disposable

A disposable syringe generally refers to a low cost single use syringe. For health and safety reasons The invention is particularly relevant to disposable syringes. Generally to keep costs down it is important that the same type of syringe is used in multiple different ways and for multiple different purposes. Therefore a mould can be made so that millions of one type of such disposable syringes can be made. This causes a range of problems which the invention is aiming to overcome.

Firstly drugs can usually not be held over time in plastic. The drugs can be affected by leaching of material out of the plastics, by leaching of the drug into the plastic and by the porosity or translucency of the syringe affecting the drug. Generally therefore it is important to retain drugs in glass ampoules. These are protective of the drugs and sealed from the manufacture and have detailed information of the drug. Therefore the first problem of the identification of the drug and dosage is provided by the notifier system.

Further it is important to have a system that can readily be altered to provide the benefits of the invention. This can be achieved by a simple alteration to the structure of the syringe but more preferably the plunger so that current syringes, and needles can be readily used but have the benefits of the present invention.

Still further the system allows the full use of the current disposable syringes but with the benefit of irremovably attachable chambers for receiving the notifier.

Example E—Pre-Filled Syringe

In a system of providing a syringe with a drug in place in a pre-filled syringe, it is necessary that various combinations of volumes and concentrations with different usages are provided due to different circumstances or different sized people or other relevant medical reasons. This requires a multitude of different pre-packaged pre-filled syringes to be made for the same drug and requires a medical user to have a range of such It is expected that usually the packaging will identify the drug and concentration. Therefore when the package is opened and the subcutaneous needle is attached to the syringe and made ready for the medical user it is resting in an unidentified state until used. In an emergency situation this has the same problems that the invention is trying to overcome.

If a particular drug is provided in a pre-filled syringe and it is open to the user to add a solute then there is no clear indication of the dosage or concentration. In this situation there are the same problems that the invention is trying to overcome.

The present invention can be used to improve this pre-filled syringe in a number of ways.

Firstly the pre-filled syringe can include a chamber for receiving a notifier. That is the drug in the syringe needs to be clearly identified and usually a plastic syringe does not provide a surface that allows clear printing like on a glass ampoule. Therefore when the drug is inserted at manufacture, the relevant notifier detailing all of the information can be By the plunger being locked to the dosage chamber and the chamber holding the notifier being locked within an end of the dosage chamber or integral with the plunger or locked alongside the dosage chamber or plunger and with the chamber holding the notifier being locked then the identification of the drug and its quantity, dosage and concentration are all duly noted and readily viewable.

Secondly the pre-filled syringe can include a particular concentration of drug. Instead of having to provide a full range of different concentrations and dosages the pre-filled syringe can be modified by inclusion of a solute. Therefore the pre-filled syringe can include a chamber into which the notifier of the modified concentrations and details of the solute can be included in a manner similar to other embodiments. The pre-filled syringe package can include a range of notifiers separately in the package or connected to the syringe and able to be frangibly removed so that the relevant notifier is inserted into the chamber when the syringe is being prepared and whenever the medical user is ready to use the pre-filled syringe can read the drug details, concentration and dosage details and know exactly what is being administered by this syringe.

Method of Use

A method of identifying an accurate dosage of medicine in a dosage chamber of a syringe including the steps of:
a) providing an accurate dosage of a detailed single dosage medicine for insertion into a dosage chamber of a syringe;
b) identifying the accurate dosage of medicine in the dosage chamber by retaining a notifier of the accurate dosage;
c) securing the notifier with the syringe
wherein the accurate dosage of medicine in a dosage chamber of a syringe is shown by the details on the notifier when secured with the syringe and allowing usage of the syringe to dispense the accurate dosage.

Figure 19:
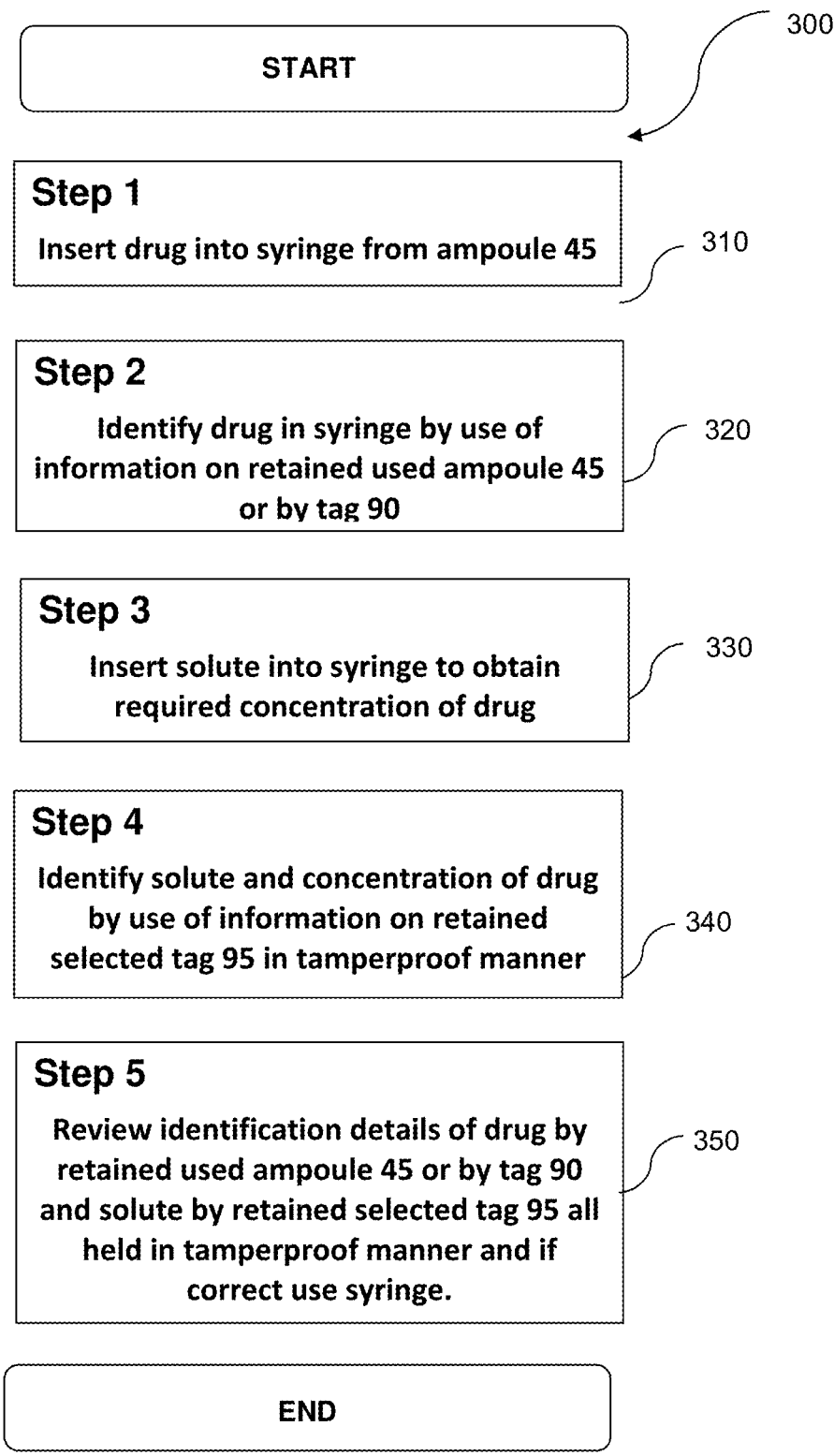
FIG. 19 is a diagrammatic view of a flow diagram of the method of usage of a syringe in accordance with an embodiment of the invention.

However as shown in more detail in FIG. 19 and illustrated in FIGS. 19 to 24 there are the five steps of the method 300 of identifying an accurate dosage of medicine in a dosage chamber of a syringe including:
  i) Step 1 of 310 in which the drug is inserted into the syringe or has been pre-filled into the syringe.
  ii) Step 2 of 320 in which Identify drug in syringe by use of information on ampoule or by tag
  iii) Step 3 of 330 in which Insert solute into syringe to obtain required concentration of drug. This step can be optional if full concentration of drug is required.
  iv) Step 4 of 340 in which Identify solute and concentration of drug and retain information in tamperproof manner; and
  v) Step 5 of 350 in which Review identification details of drug and solute and if correct use syringe.

Figure 20:
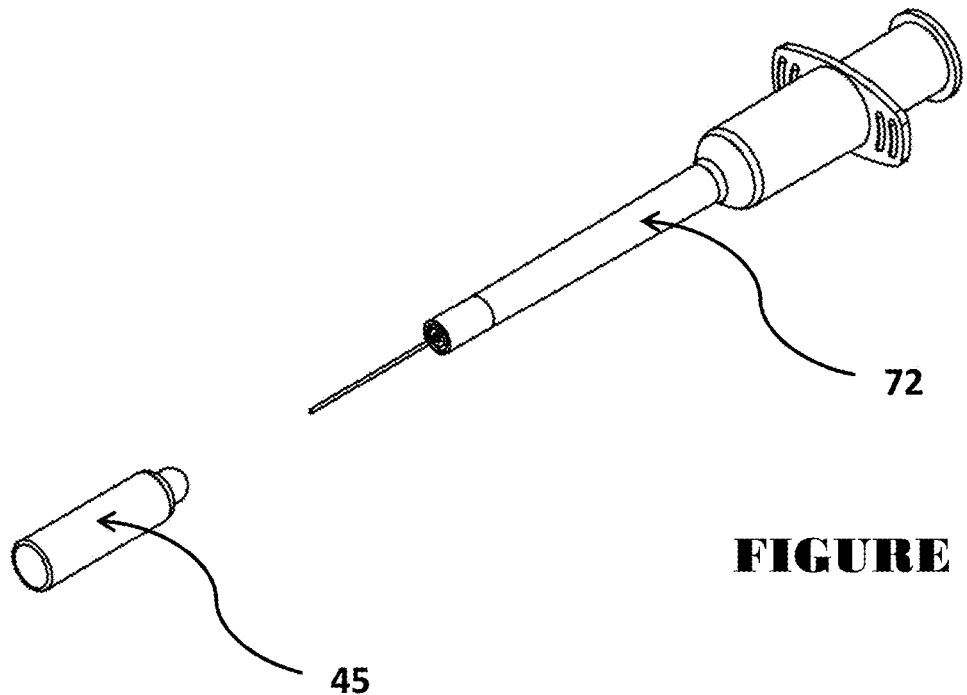
FIGS. 20 to 24 are diagrammatic views of examples of steps 1 to 5 of the message of usage of the syringe of FIG. 19.
Figure 20:
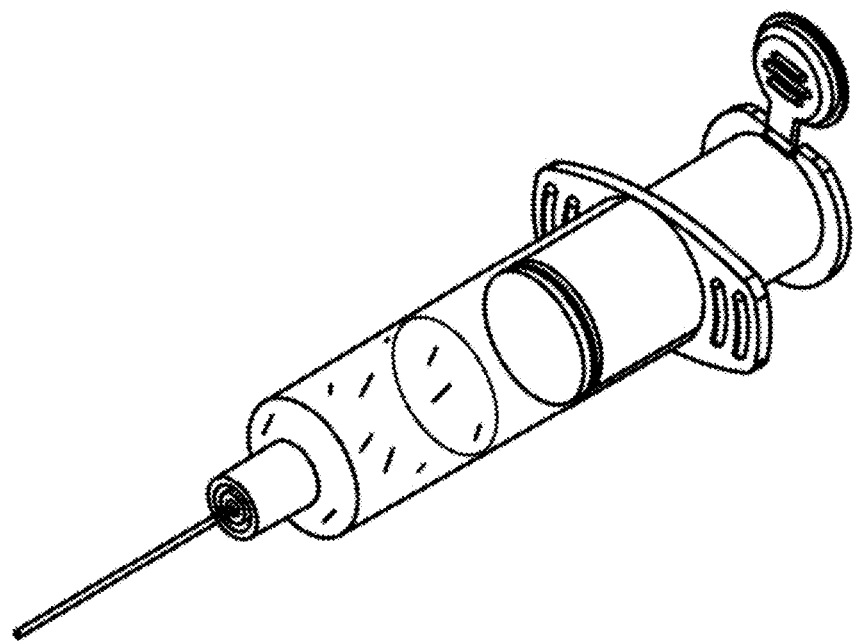
Figure 21:
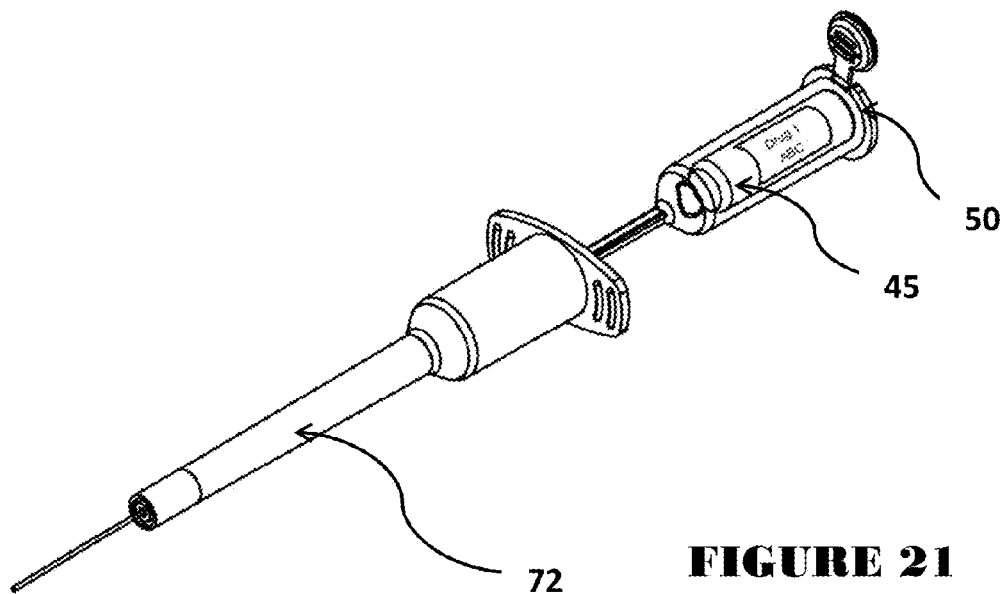
Figure 22:
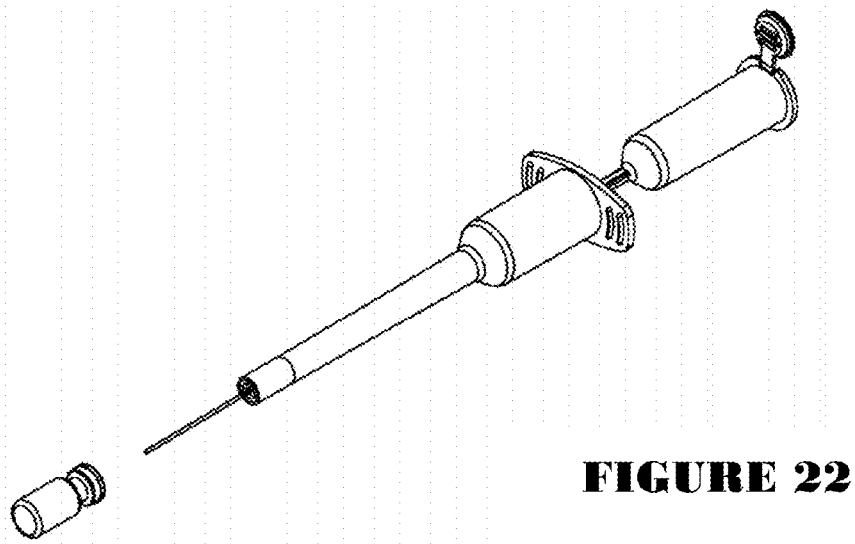
Figure 23:
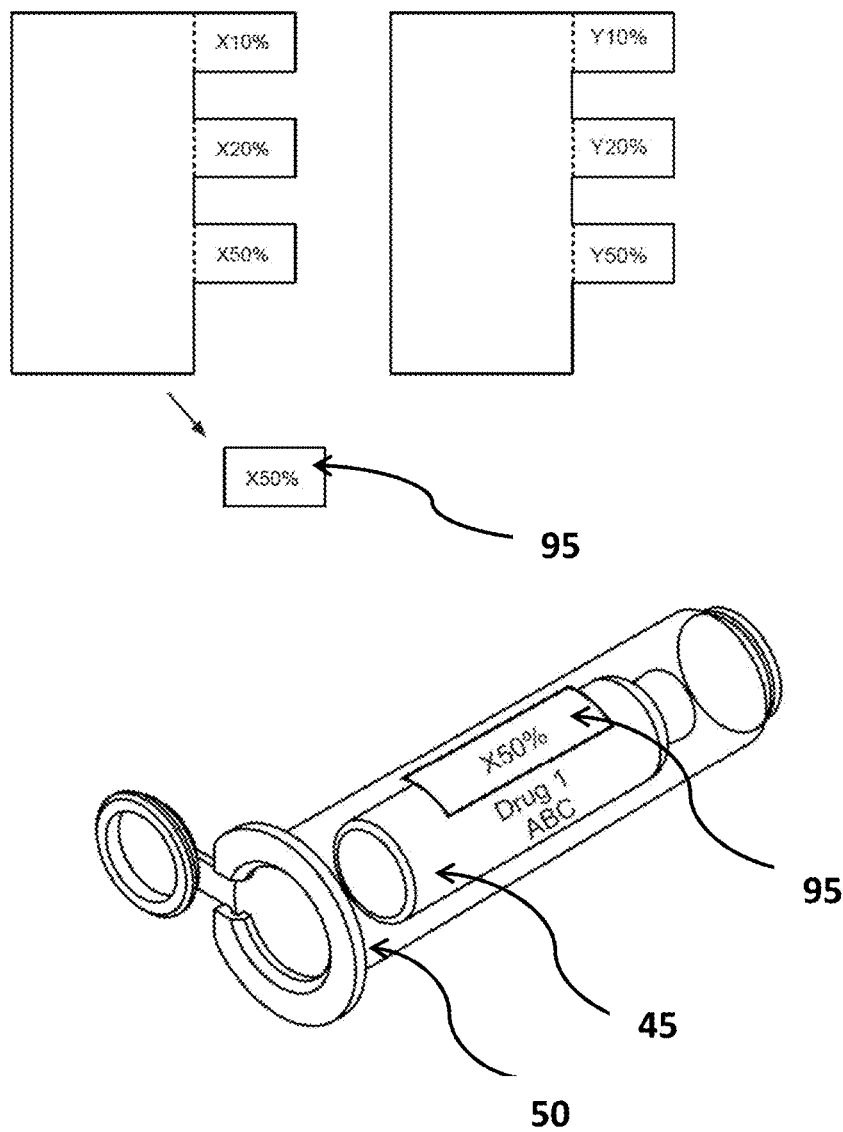
Figure 24:
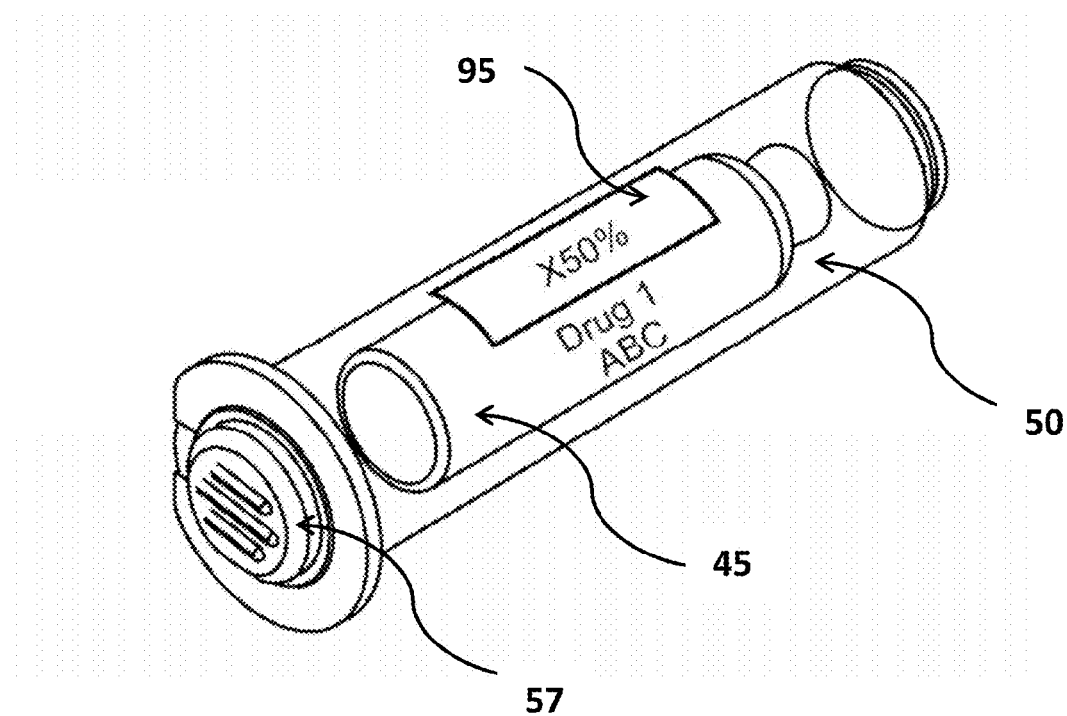

The step of providing an accurate dosage of a detailed single dosage medicine includes providing the medicine in a frangible medicine container for insertion into a dosage chamber of a syringe and the frangible medicine container includes detailed information of the medicine. Usually the frangible medicine container is an ampoule and the step 2 of identifying an accurate dosage of medicine in the dosage chamber is by retaining the medicine container after being used in a receiving chamber on the syringe. Therefore as shown in FIG. 20 the drug is inserted into the syringe or has been pre-filled into the syringe.

However identifying the accurate dosage of medicine in the dosage chamber is by retaining at least one notifier matching the accurate dosage in a receiving chamber on the syringe. Therefore in FIG. 20 this is achieved by retaining the used ampoule in the receiving chamber. If the dosage chamber is prefilled at manufacture then the information needs to be transferred to be unequivocally connected with the syringe. A tag having those details could be included in the packaging or pre-inserted in the receiving chamber of the drug pre-filled syringe.

The identifying of the accurate dosage of medicine in the dosage chamber is also by retaining at least one notifier identifying the solute in the dosage chamber by an identifier. Therefore in step 3 the solute is introduced into the Therefore the step 4 of the method is identifying of the accurate dosage of medicine in the dosage chamber by retaining two notifiers, one identifying the medicine and one identifying the solute in the dosage chamber by an identifier wherein the accurate dosage of medicine in a dosage chamber of a syringe is shown by the details on the single dosage medicine and the identifier on the solute.

However an important point is that when a medical user wishes to undertake Step 5 they wish to know that there is no error or tampering since the earlier steps were undertaken. Therefore the identifying of the accurate dosage of medicine in the dosage chamber by retaining at least one notifier identifying the solute in the dosage chamber by an identifier in a receiving chamber and securing the at least one notifier within the chamber. This lid to the chamber is tamperproof and not openable after insertion of the notifiers.

It can be seen that the invention can be provided in a number of ways to provide the substantial benefits and the invention is not limited to the examples.

Interpretation

Embodiments

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.
Different Instances of Objects As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.
Specific Details In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.
Comprising and Including In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the syringe usage industries including medical centres such as hospitals, doctor's surgeries but a particularly important industry is the medical emergency industry including mobile medical treatment units, ambulances, mobile military units, etc. However it is also important in domestic, schools and commercial situations where disposable use occurs or minimal trained medical users require an effective and efficient and safe syringe usage.

What is claimed is:

1. A syringe, comprising:
a dosage chamber having a dispensing opening for receiving and dispensing a dosage of medicine therefrom, and a plunger opening for receiving a plunger;
a plunger located in the plunger opening and movable within the dosage chamber to enable partial withdrawal of the plunger from the dosage chamber to draw a medicine from a medicine container through the dispensing opening and into the dosage chamber, and subsequent partial or complete insertion of the plunger into the dosage chamber to dispense the medicine from the dosage chamber through the dispensing opening, said plunger comprising a longitudinal shaft;
a verification chamber comprising a transparent cylindrical chamber sized to receive the medicine container through an opening at a proximal end thereof and sized to fit within the dosage chamber, wherein the verification chamber is closed at a distal end thereof, which is integral with or permanently fixed to the proximal end of the longitudinal shaft of the plunger, wherein the proximal end is an end closer to the plunger opening and a distal end is an end closer to the dispensing opening, wherein the verification chamber is configured to receive the medicine container in a used state; and
a tamperproof locking mechanism operable to prevent removal of the medicine container from the verification chamber;
wherein the verification chamber is configured to allow visual inspection of the medicine container locked within the verification chamber so that the medicine that was drawn from the open ampoule into the dosage chamber can be securely identified and verified by visual inspection of an identifier of the medicine container locked within the verification chamber.

2. The syringe according to claim 1, wherein the medicine container is of a type that has a frangible seal that is broken to access the medicine stored therein, and the verification chamber acts as a sharps container to protect a user of the syringe from a broken seal of the medicine container locked within the verification chamber.

3. The syringe according to claim 2, wherein the medicine container is an ampoule.

4. The syringe or assembly according to claim 1, wherein the verification chamber includes a transparent window to allow visual inspection of the medicine container locked within the verification chamber.

5. The syringe or assembly according to claim 1, wherein the verification chamber contains an identifier of the medicine in the dosage chamber, and an identifier of a solute in the dosage chamber.

6. The syringe or assembly according to claim 2, wherein the verification chamber contains an identifier of the medicine in the dosage chamber, and an identifier of a solute in the dosage chamber.

7. The syringe or assembly according to claim 3, wherein the verification chamber contains an identifier of the medicine in the dosage chamber, and an identifier of a solute in the dosage chamber.

8. The syringe or assembly according to claim 4, wherein the verification chamber contains an identifier of the medicine in the dosage chamber, and an identifier of a solute in the dosage chamber.

9. The syringe or assembly according to claim 1, wherein the tamperproof locking mechanism includes an entrapment mechanism or a one way ratchet means.

10. The syringe or assembly according to claim 2, wherein the tamperproof locking mechanism includes an entrapment mechanism or a one way ratchet means.

11. The syringe or assembly according to claim 3, wherein the tamperproof locking mechanism includes an entrapment mechanism or a one way ratchet means.

12. The syringe or assembly according to claim 4, wherein the tamperproof locking mechanism includes an entrapment mechanism or a one way ratchet means.

13. The syringe or assembly according to claim 5, wherein the tamperproof locking mechanism includes an entrapment mechanism or a one way ratchet means.

14. The syringe or assembly according to claim 6, wherein the tamperproof locking mechanism includes an entrapment mechanism or a one way ratchet means.

15. The syringe or assembly according to claim 7, wherein the tamperproof locking mechanism includes an entrapment mechanism or a one way ratchet means.

16. The syringe or assembly according to claim 8, wherein the tamperproof locking mechanism includes an entrapment mechanism or a one way ratchet means.

17. A method of identifying a medicine in or dispensed from a dosage chamber of a syringe according to claim 1, comprising:

drawing the dosage of medicine from the medicine container into the dosage chamber of the syringe by partial withdrawal of the plunger of the syringe from the dosage chamber;

inserting the medicine container into the verification chamber of the syringe; and operating the tamperproof locking mechanism to prevent removal of the medicine container from the verification chamber, visually inspecting an identifier of the medicine container locked within the verification chamber so as to securely identify and verify that the medicine that was drawn from the medicine container into the dosage chamber.

18. The method according to claim 17, wherein the medicine container is of a type that has a frangible seal that is broken to access the medicine stored therein, and the verification chamber acts as a sharps container to protect a user of the syringe from a broken seal of the medicine container locked within the verification chamber.

19. The method according to claim 18, wherein the medicine container is an ampoule.

20. A syringe, comprising:

a dosage chamber having a dispensing opening for receiving and dispensing a dosage of medicine therefrom, and a plunger opening for receiving a plunger;

a plunger located in the plunger opening and movable within the dosage chamber to enable partial withdrawal of the plunger from the dosage chamber to draw a medicine from a medicine container through the dispensing opening and into the dosage chamber, and subsequent partial or complete insertion of the plunger into the dosage chamber to dispense the medicine from the dosage chamber through the dispensing opening, said plunger comprising a longitudinal shaft;

a verification chamber comprising a transparent cylindrical chamber sized to receive the medicine container through an opening at a proximal end thereof and sized to fit within the dosage chamber, wherein the verification chamber is closed at a distal end thereof, which is integral with or permanently fixed to the proximal end of the longitudinal shaft of the plunger, wherein the proximal end is an end closer to the plunger opening and a distal end is an end closer to the dispensing opening, wherein the verification chamber is configured to receive the medicine container in a used state; and a tamper-resistant closure operable to block the opening of the verification chamber and prevent or at least inhibit removal of the medicine container from the verification chamber;

wherein the verification chamber is configured to allow visual inspection of the medicine container locked within the verification chamber so that the medicine that was drawn from the open ampoule into the dosage chamber can be securely identified and verified by visual inspection of an identifier of the medicine container locked within the verification chamber.

21. A kit comprising the syringe of claim 1 and the medicine container containing the medicine from which the dosage of medicine is drawn.

* * * * *

UNITED STATES PATENT AND TRADEMARK OFFICE
CERTIFICATE OF CORRECTION

PATENT NO. : 10,500,343 B2
APPLICATION NO. : 15/528762
DATED : December 10, 2019
INVENTOR(S) : George Poulos Page 1 of 2

It is certified that error appears in the above-identified patent and that said Letters Patent is hereby corrected as shown below:

In the Specification

In Column 1, Line 12, after "1.57" insert --.--.

In Column 3, Line 28, delete "claim 10, wherein" and insert --some embodiments herein,--.

In Column 5, Line 53, after "30" insert --.--.

In Column 5, Line 59, before "an" delete "a".

In Column 7, Lines 4-5, delete "This C-clamp can include a locking means to prevent removal from the dosage chamber." and insert the same on Column 7, Line 3 as a continuation of same paragraph.

In Column 8, Line 41, after "syringe" insert --.--.

In Column 12, Line 36, delete "For health and safety reasons".

In Column 13, Line 6, after "such" insert --pre-filled syringes.--.

In Column 14, Line 2, after "tag" insert --.--.

In Column 14, Line 35, after "into the", insert --dosage chamber.--.

In the Claims

In Column 17, Line 14 (Approx.), Claim 4, delete "syringe or assembly" and insert --syringe--.

In Column 17, Line 18 (Approx.), Claim 5, delete "syringe or assembly" and insert --syringe--.

Signed and Sealed this
Twenty-fifth Day of August, 2020

Andrei Iancu
*Director of the United States Patent and Trademark Office*

CERTIFICATE OF CORRECTION (continued)
U.S. Pat. No. 10,500,343 B2

In Column 17, Line 22 (Approx.), Claim 6, delete "syringe or assembly" and insert --syringe--.

In Column 17, Line 26 (Approx.), Claim 7, delete "syringe or assembly" and insert --syringe--.

In Column 17, Line 30 (Approx.), Claim 8, delete "syringe or assembly" and insert --syringe--.

In Column 17, Line 34 (Approx.), Claim 9, delete "syringe or assembly" and insert --syringe--.

In Column 17, Line 37 (Approx.), Claim 10, delete "syringe or assembly" and insert --syringe--.

In Column 17, Line 40 (Approx.), Claim 11, delete "syringe or assembly" and insert --syringe--.

In Column 17, Line 43 (Approx.), Claim 12, delete "syringe or assembly" and insert --syringe--.

In Column 17, Line 46 (Approx.), Claim 13, delete "syringe or assembly" and insert --syringe--.

In Column 17, Line 49 (Approx.), Claim 14, delete "syringe or assembly" and insert --syringe--.

In Column 17, Line 52 (Approx.), Claim 15, delete "syringe or assembly" and insert --syringe--.

In Column 17, Line 55 (Approx.), Claim 16, delete "syringe or assembly" and insert --syringe--.